United States Patent [19]

Das et al.

[11] Patent Number: 4,550,120
[45] Date of Patent: Oct. 29, 1985

[54] 7-OXABICYCLOHEPTANE SUBSTITUTED ETHERS AND THEIR USE IN TREATING THROMBOLYTIC DISEASE

[75] Inventors: Jagabandhu Das, Plainsboro; Steven E. Hall, Ewing Township, Mercer County, both of N.J.

[73] Assignee: E. R. Squibb & Sons, Inc., Princeton, N.J.

[21] Appl. No.: 605,535

[22] Filed: Apr. 30, 1984

[51] Int. Cl.[4] .................. A61K 31/34; A61K 31/557; C07D 307/00
[52] U.S. Cl. ..................... 514/469; 549/463
[58] Field of Search .................. 549/463; 424/285; 514/469

[56] References Cited

U.S. PATENT DOCUMENTS

| | | | |
|---|---|---|---|
| 4,143,054 | 3/1979 | Sprague | 549/463 |
| 4,187,236 | 2/1980 | Sprague | 549/463 |
| 4,220,594 | 9/1980 | Sprague | 549/463 |
| 4,228,180 | 10/1980 | Sprague | 549/463 |
| 4,254,044 | 3/1981 | Sprague | 549/463 |

FOREIGN PATENT DOCUMENTS 0043292 8/1982 European Pat. Off. .
2039909 8/1980 United Kingdom .

*Primary Examiner*—Henry R. Jiles
*Assistant Examiner*—Bernard I. Dentz
*Attorney, Agent, or Firm*—Lawrence S. Levinson; Burton Rodney

[57] ABSTRACT

7-Oxabicycloheptane substituted ether prostaglandin analogs are provided having the structural formula

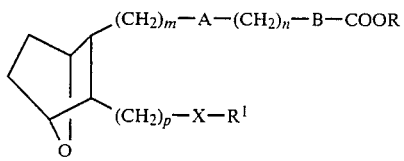

wherein A is O or

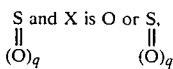

and X is O or S, and including all stereoisomers thereof.

The compounds are cardiovascular agents useful, for example, in the treatment of thrombolytic disease.

15 Claims, No Drawings

7-OXABICYCLOHEPTANE SUBSTITUTED ETHERS AND THEIR USE IN TREATING THROMBOLYTIC DISEASE

DESCRIPTION OF THE INVENTION

The present invention relates to 7-oxabicycloheptane substituted ether prostaglandin analogs which are cardiovascular agents useful, for example, in the treatment of thrombolytic disease. These compounds have the structural formula

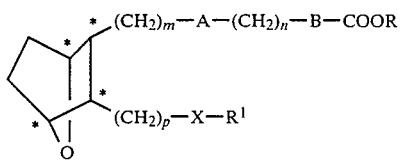

and including all stereoisomers thereof,
wherein A is O or

B is a single bond or —CH═CH—, m is 1 or 2, n is 1 to 8, p is 1 to 5, X is O or

wherein q is 0, 1 or 2 when A is 0 (oxygen) and q is 0 (zero) when A is S; R is H, lower alkyl, alkali metal or tris(hydroxymethyl)amino methane and $R^1$ is lower alkyl, aryl, aralkyl, cycloalkyl, cycloalkylalkyl or lower alkenyl.

Thus, the compounds of the invention include the following types of compounds:

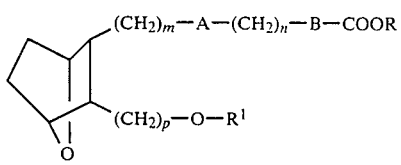

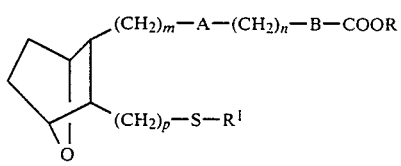

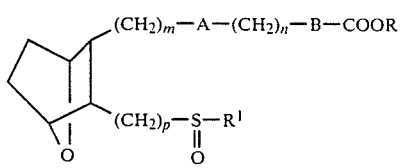

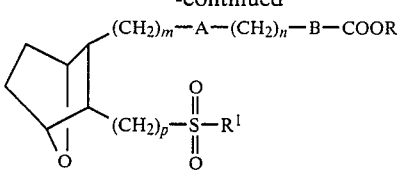

The term "lower alkyl" or "alkyl" as employed herein includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, an alkyl-aryl substituent, a haloaryl substituent, a cycloalkyl substituent or an alkylcycloalkyl substituent.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or lower alkoxy groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, halogens (Cl, Br or F), and/or lower alkoxy groups.

The term "aralkyl", "aryl-alkyl" or "aryl-lower alkyl" as used herein refers to lower alkyl groups as discussed above having an aryl substituent, such as benzyl.

The term "lower alkenyl" as used herein refers to straight or branched chain radicals of 2 to 12 carbons, preferably 2 to 6 carbons in the normal chain, which include one double bond in the normal chain, such as 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl and the like.

The term "halogen" or "halo" as used herein refers to chlorine, bromine, fluorine or iodine, with chlorine being preferred.

The terms "$(CH_2)_m$", "$(CH_2)_n$" and "$(CH_2)_p$" includes a straight or branched chain radical having 1 or 2 carbons in the normal chain in the case of $(CH_2)_m$, 1 to 8 carbons in the normal chain in the case of "$(CH_2)_n$" and 1 to 5 carbons in the normal chain in the case of "$(CH_2)_p$" and may contain one or more lower alkyl substituents. Examples of $(CH_2)_m$, $(CH_2)_n$ and $(CH_2)_p$ groups include $$CH_2, CH, -CH-, CH_2CH_2, (CH_2)_3, (CH_2)_4,$$
$$\phantom{CH_2, CH,}|\phantom{-CH-,}|$$
$$\phantom{CH_2, CH, -CH-, }C_2H_5\phantom{CH,}CH_3$$

$$(CH_2)_5, (CH_2)_6, (CH_2)_7, -(CH_2)_2-CH-, -CH_2-CH-,$$
$$\phantom{(CH_2)_5, (CH_2)_6, (CH_2)_7, -(CH_2)_2-}|\phantom{-, -CH_2-}|$$
$$\phantom{(CH_2)_5, (CH_2)_6, (CH_2)_7, -(CH_2)_2-}CH_3\phantom{-, -CH_2-}CH_3$$

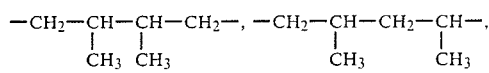

and the like.

Preferred are those compounds of formula I wherein m is 1, A is O or S, n is 3 to 5, B is a single bond, p is 1, X is O or S, R is H, and R¹ is lower alkyl, such as hexyl, aryl, such as phenyl, or aralkyl such as benzyl.

The various compounds of the invention may be prepared as outlined below.

The 7-oxabicycloheptane ether compounds of formula I of the invention wherein X is O, m is 2, p is 1 A is O, n is 1 to 8 and B is a single bond that is

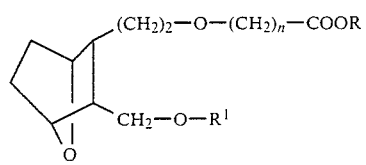

IE may be prepared starting with the cyanoalcohol II

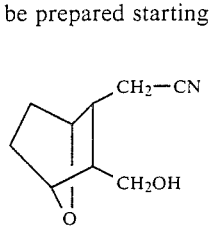

II which is subjected to a benzylation wherein compound II is reacted with a base such as NaH, NaOCH₃, KH, KOt—C₄H₉ and the like in the presence of an inert solvent, such as dimethylformamide, dimethoxyethane or tetrahydrofuran to form the mono benzylether compound III

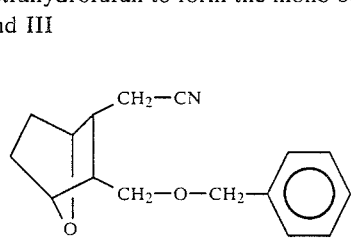

III

Compound III is reduced with diisobutyl aluminum hydride in the presence of an inert solvent, such as tetrahydrofuran, toluene or methylene chloride, to form the aldehyde IV

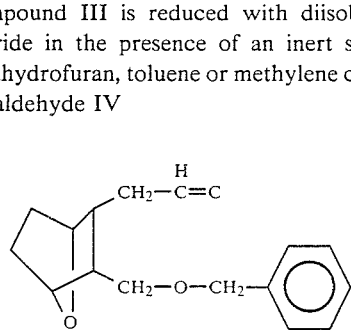

IV which may then be reduced by reaction with lithium aluminum hydride to form the alcohol V

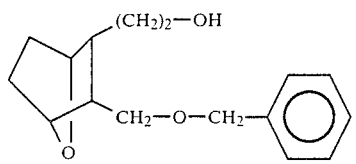

V

Compound V is then used to prepare the final products wherein m is 2 as will be described hereinafter.

The 7-oxabicycloheptane ether compounds of formula I of the invention wherein m is 1, n is 1 to 8, B is a single bond, and p is 1, that is,

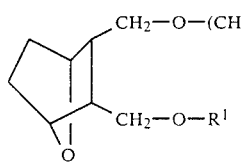

IF may be prepared by subjecting the diol VI

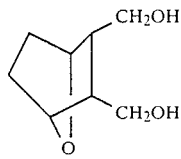

VI to a benzylation wherein compound VI is reacted with a base such as NaH, NaOCH₃, KH, KOt—C₄H₉ and the like and a benzyl halide such as benzylbromide in the presence of an inert solvent such as dimethylformamide, dimethoxyethane, tetrahydrofuran or benzene to form the monobenzylether VII

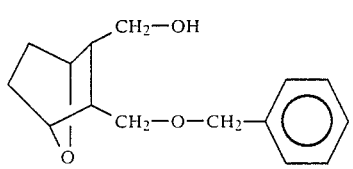

VII which is used to prepare compounds of formula I wherein (CH₂)ₘ is CH₂ as described hereinafter.

Compound V or VII herein referred to as compounds V-VII, that is

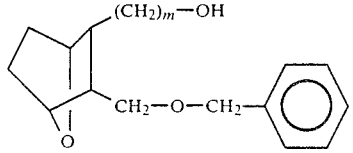

V-VII (wherein m is 2 where compound V is used and m is 1 where compound VII is used)

is subjected to O-alkylation wherein it is reacted with a base such as KOH or NaOH and a silyl compound of the structure

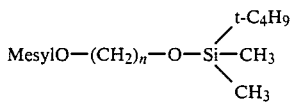

in the presence of an aromatic solvent such as xylene, toluene or mesitylene to form the silyl compound VIII

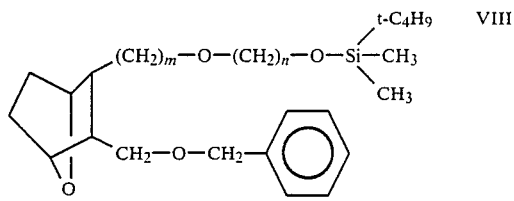

(m is 2 if V is used as the starting material or m is 1 if VII is used as the starting material)
which is desilylated by reacting same with tetra-n-butyl ammonium fluoride in the presence of an inert solvent such as tetrahydrofuran, or 40% aqueous hydrofluoric acid in tetrahydrofuran to form the alcohol IX

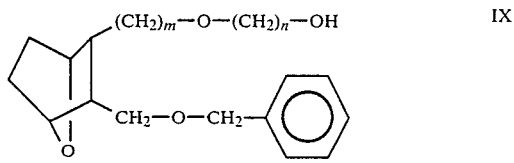

(wherein m is 2 or 1)
The alcohol IX is then made to undergo a Jones oxidation by reacting IX with chromium trioxide or other oxidizing agent such as pyridinium dichromate, in the presence of acetone or dimethylformamide to form the acid X, which by themselves are compounds in accordance with the invention as defined in formula I

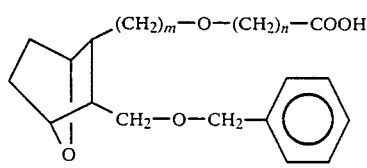

(where m is 2 or 1)
Acid X is then subjected to esterification by reacting acid X with diazomethane or other esterifying agent of the structure $RCHN_2$ (where R is an alkyl group) to form the ester XI, which themselves are in accordance with the present invention and are within the scope of formula I

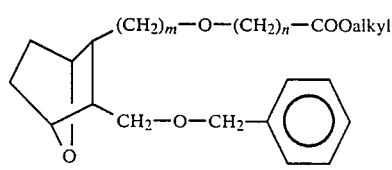

(wherein m is 2 or 1)
Ester XI is then subjected to hydrogenolysis by reacting ester XI with hydrogen in the presence of a catalyst such as palladium on carbon, platinum oxide and the like to form the alcohol XII

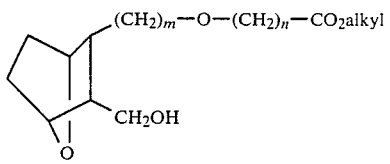

(wherein m is 2 or 1)
Other compounds of the invention within the scope of formula I may be prepared from alcohol XII as follows.

The alcohol XII is subjected to an ether formation reaction wherein XII is reacted with a strong base such as KOH, NaOH or LiOH in the presence of an inert organic solvent such as xylene, toluene, benzene or mesitylene, and then after partial removal of solvent, reacting with a sulfonate compound of the structure

or a halide of the structure

wherein X is Cl or Br, to form the ether IG

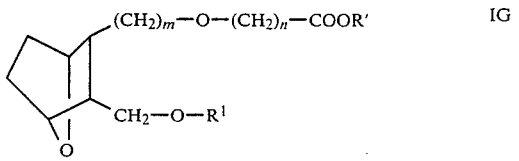

Ether IG is then hydrolyzed by treating with strong base such as LiOH, KOH or NaOH to form the corresponding alkali metal salt and then neutralizing with a strong acid such as HCl or oxalic acid to form IH

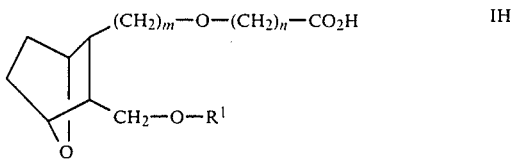

Compounds of the invention wherein B is —CH=CH—, that is, compounds of IJ

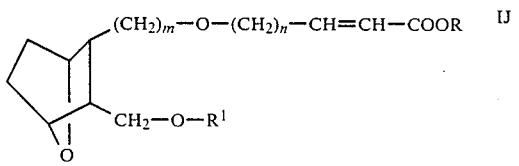

(where m is 2 or 1)
may be prepared by subjecting the alcohol XIII which covers alcohol VII or V,

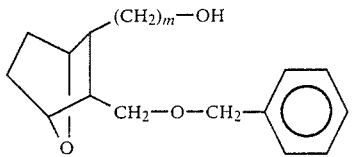
XIII to O-alkylation wherein XIII is reacted with a base such as KOH, NaOH and a silyl compound

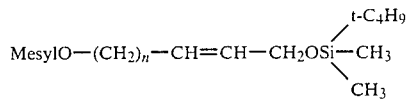
C in the presence of an aromatic solvent such as xylene, toluene or mesitylene, to form the silyl compound XIV

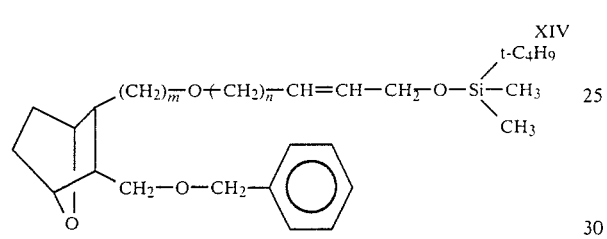
XIV

Compound XIV is desilylated by reacting same with tetra-n-butyl ammonium fluoride in the presence of an inert solvent such as tetrahydrofuran, or with 40% aqueous hydrofluoric acid in tetrahydrofuran to form the alcohol XV

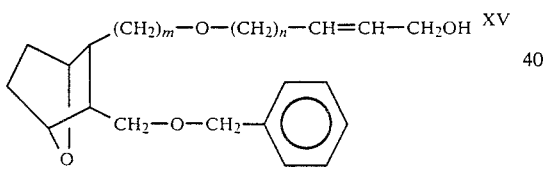
XV which is then subjected to a Jones oxidation as described hereinbefore with respect to alcohol IX to form the acid XVI

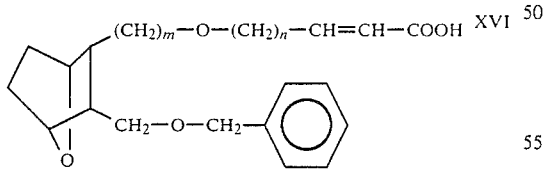
XVI which is esterified as described hereinbefore with respect to acid X to form the ester XVII

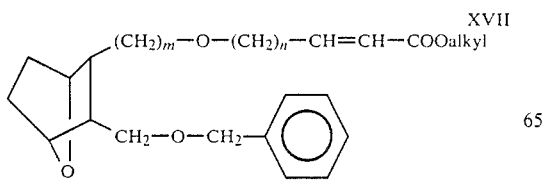
XVII

Ester XVII is then subjected to hydrogenolysis as described with respect to ester XI to form the alcohol XVIII

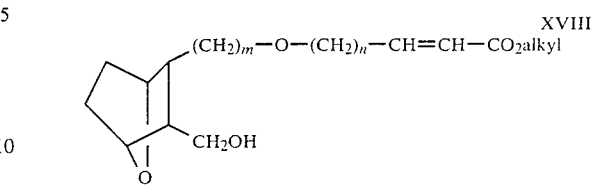
XVIII and the alcohol XVIII is converted to the compounds of the invention via an ether formation reaction by reaction with base and A, A′ or $R^1X$, as described hereinbefore, to form ether IF which may be hydrolyzed as described above to the corresponding alkali metal salt and then the acid

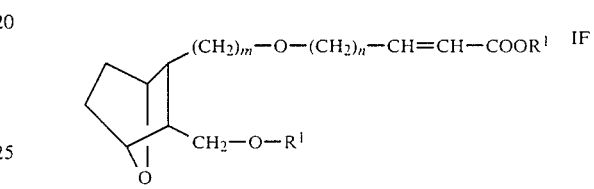
IF

Compounds of formula I wherein A is S, m is 2, n is 1 to 8 and B is a single bond, that is

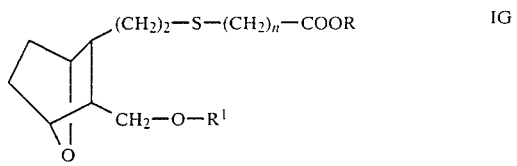
IG may be prepared starting with the cyanoalcohol II

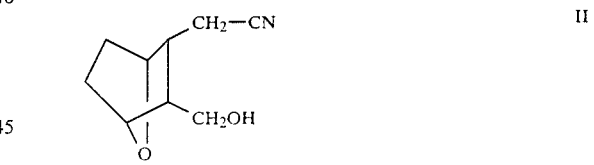
II which is subjected to a silylation wherein compound II is reacted with a t-butyldimethylsilyl chloride having the structure D

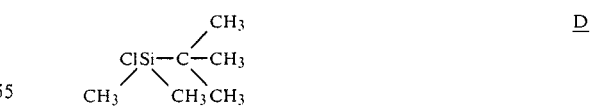
D in the presence of dry dichloromethane and triethylamine and 4-dimethylaminopyridine to form the silyl ether XIX

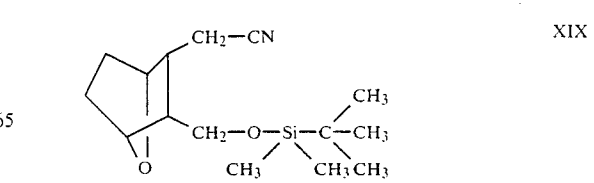
XIX which is reduced by treating with a reducing agent such as diisobutylaluminum hydride, in the presence of an inert organic solvent such as toluene, tetrahydrofuran or methylene chloride in an inert atmosphere, at reduced temperatures of from about −78° C. to about 0° C. to form the aldehyde XX

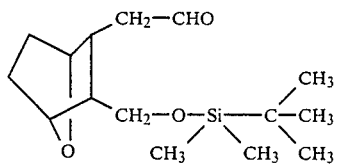
XX

The aldehyde XX is further reduced by treatment with a reducing agent such as lithiumaluminum hydride, sodium borohydride or lithium borohydride in the presence of an inert organic solvent such as tetrahydrofuran, ethanol or ether to form the alcohol XXI

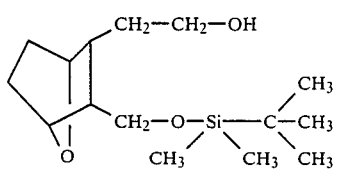
XXI

The alcohol XXI is then subjected to a modified Mitsonubu reaction wherein a mixture of the alcohol V and thiolacetic acid in an inert solvent such as tetrahydrofuran, ether or toluene is reacted with a mixture of triphenylphosphine and diisopropylazo dicarboxylate in an inert organic solvent such as tetrahydrofuran, ether or toluene at reduced temperatures of from about 0° C. to about 25° C. to form thioacetate XXII

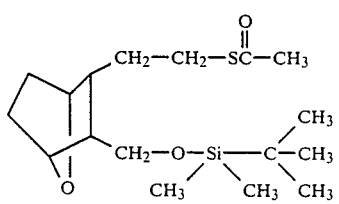
XXII

The silyl group is removed from thioacetate XXII by reacting VI with tetra-n-butylammonium fluoride trihydrate in the presence of an inert organic solvent such as tetrahydrofuran or ether to form alcohol thioacetate XXIII

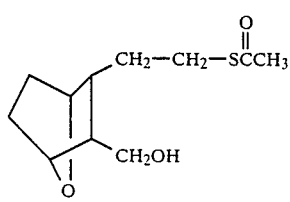
XXIII which is then deacetylated by treating with lithium aluminum hydride, potassium carbonate or sodium methoxide in the presence of an inert organic solvent such as tetrahydrofuran or methanol to form thiol XXIV

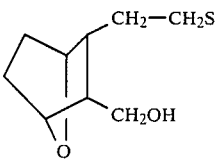
XXIV

The thiol XXIV is then alkylated by reacting same with an alkylating agent of the structure XXV

Hal—$(CH_2)_n$—B—$CO_2$alkyl       XXV in the presence of a base such as sodium or potassium carbonate in the case where B is —CH=CH—, or sodium or potassium hydride in the case where B is a single bond, and an inert organic solvent such as acetone, THF or DMF, and reduced temperatures of from about 0° C. to about 50° C., to form alcohol XXVI

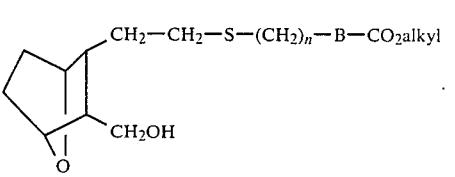
XXVI

The alcohol XXVI may be converted to the ethers of formula I via an ether formation reaction followed by hydrolysis as described above with respect to alcohol XII.

Alternatively, compounds of the invention wherein n is 3 or more and B is a single bond may be prepared by reacting thiol XXIV with an alkylating agent of the structure E

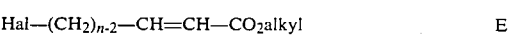
Hal—$(CH_2)_{n-2}$—CH=CH—$CO_2$alkyl       E in the presence of a base such as $Na_2CO_3$, sodium hydride, or K t-butoxide as described above to form alcohol XXVII

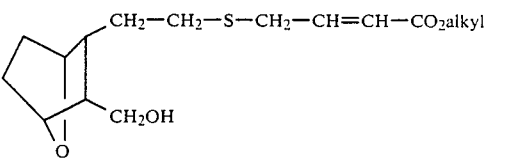
XXVII which may be hydrogenated by reaction with hydrogen in the presence of a catalyst such as palladium on charcoal in methanol to form the saturated ester XXVIII

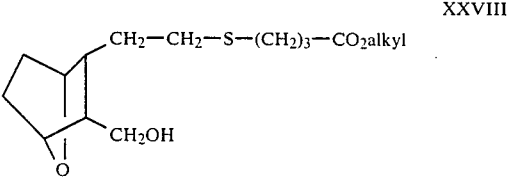
XXVIII

Then following the reaction sequence (as described above with respect to alcohol XII), the ethers of formula I are formed wherein n is 3 or more and B is a single bond.

Compounds of the invention wherein $(CH_2)_m$ is $CH_2$, A is S, B is $CH=CH$, p is 1 and n is 1 to 8 may be prepared by subjecting alcohol XXIX

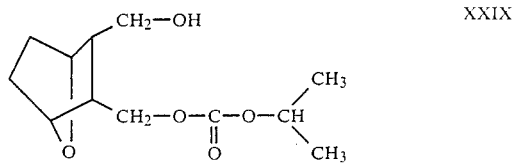

to a modified Mitsonubu reaction as described above with respect to alcohol XXI to form thioacetate XXX

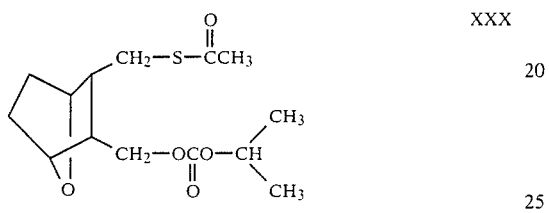

which is then reduced by treating with lithium aluminum hydride or diborane in the presence of an inert organic solvent such as tetrahydrofuran or other solvent such as ether to form the thiol XXXII

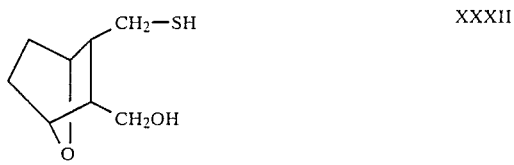

Thiol XXXII is then alkylated by reacting with alkylating agent XXV

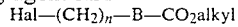
$Hal-(CH_2)_n-B-CO_2alkyl$     XXV as described above with respect to thiol XXIV to form alcohol XXXIII

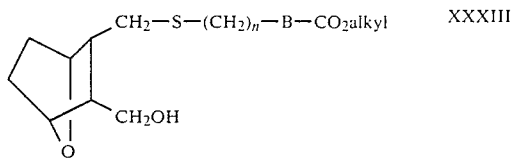

The compounds of formula XXXIII wherein B is a single bond, that is

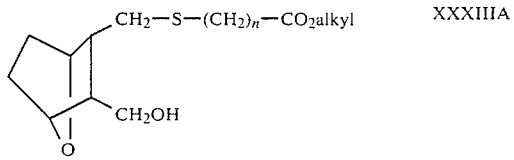

may be prepared from XXXIII by reducing XXXIII by treatment with hydrogen in the presence of palladium on charcoal.

Then following the reaction sequence as described above with respect to alcohol XII (and alcohol XXVIII), the ethers of formula I are formed wherein B is $-CH=CH-$ or a single bond.

Compounds of formula I wherein X is S, A is S or O, m is 1 or 2, p is 1 and B is a single bond may be prepared by starting with the hydroxymethyl compound XII

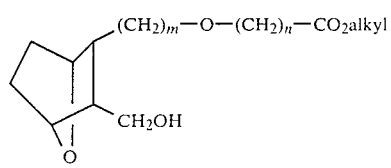

(wherein m is 2 or 1)
compound XVIII

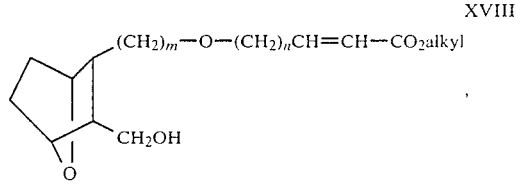

(wherein m is 2 or 1)
compound XXVI

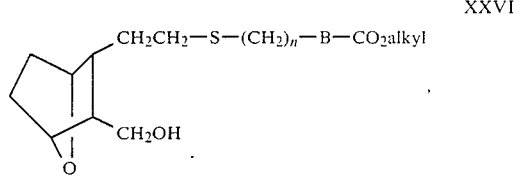

(including compounds XXVII and XXVIII)
compound XXXIII

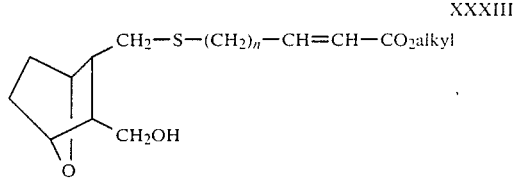

compounds XXXIIIA

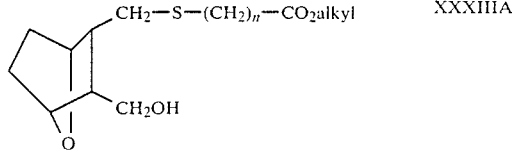

and subjecting one of the above hydroxymethyl compounds to a tosylation reaction, for example, by reacting the hydroxymethyl compound with tosyl chloride in pyridine and methylene chloride to form the corresponding tosylate XXXIV

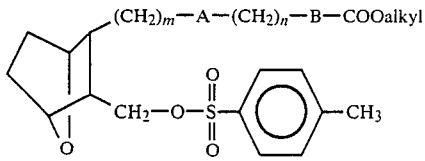 XXXIV

Thereafter, tosylate XXXIV is reacted with a thiol or mercaptan of the structure F

HSR[1]  F in the presence of potassium t-butoxide and a solvent such as tetrahydrofuran, dimethyl sulfoxide or dimethylformamide to form compounds of the invention of the structure XXXV

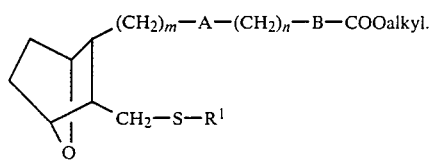 XXXV

Compounds of formula I wherein B is a single bond or —CH=CH—, m is 1 and p is 2 to 5 may be prepared by subjecting aldehyde XXXVI

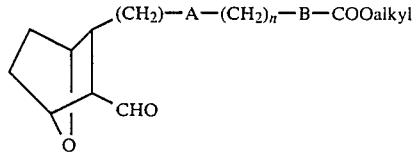 XXXVI wherein A is O or S
to a homologation sequence, such as a Wittig reaction with $(C_6H_5)_3P^+Cl^-CH_2OCH_3$ followed by hydrolysis, (p-1) times, to form aldehyde XXXVII

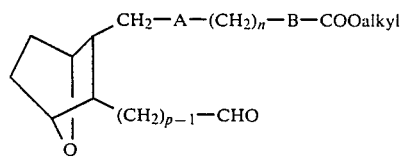 XXXVII which is carried on to compounds of the invention where p is 2 to 5 by reducing aldehyde XXXVII employing a reducing agent such as sodium borohydride in a solvent such as methanol to form alcohol ester XXXVIII

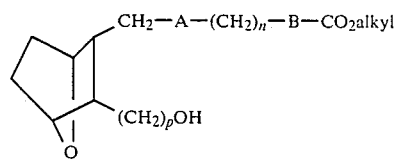 XXXVIII which is subjected to an etherification reaction with B, B' or B'' as described above or to a thioetherification reaction with thiol F to form XXXIX

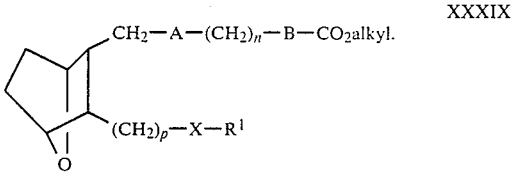 XXXIX

Aldehyde XXXVI wherein A is O may be prepared from alcohols XII and XVIII (wherein A is O) by carrying out a Collins oxidation wherein alcohol XII is reacted with $CrO_3$ in the presence of an organic base such as pyridine, in dichloromethane or with pyridinium chlorochromate in a solvent such as methylene chloride.

Aldehyde XXXVI wherein A is S may be prepared from alcohol XXXIII (wherein A is S) by subjecting such alcohols to a Corey-Kim oxidation wherein the appropriate alcohol in toluene is added to a mixture of dimethylsulfide and N-chlorosuccinimide in dry toluene or other inert organic solvent such as methylene chloride, and the mixture is stirred at 0° C. and then cooled to −25° C. After stirring at −25° C., triethylamine is added and the mixture is then warmed and concentrated to give aldehyde XXXVI.

Compounds of the invention wherein m is 2 and p is 2, 3, 4, or 5 may be prepared by oxidizing alcohol XVIII (wherein A is O) via a Collins oxidation technique as described hereinbefore or by oxidizing alcohol XXVI or XXVIII (wherein A is S) via a Corey-Kim oxidation or Swern oxidation as described hereinbefore to form aldehyde XL

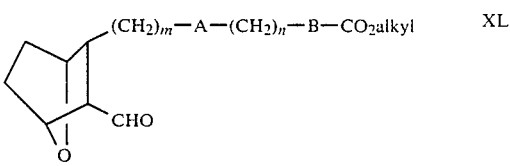 XL

Aldehyde XL is then subjected to a homologation sequence such as a Wittig reaction with $(C_6H_5)_3P^+Cl^-CH_2OMe$ followed by hydrolysis, (p-1) times, to form aldehyde XLI

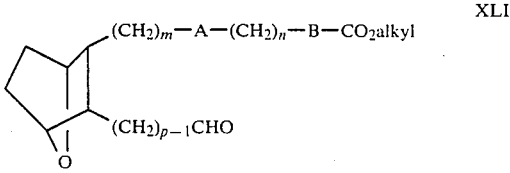 XLI

Aldehyde XLI is then reduced to the corresponding alcohol XLII

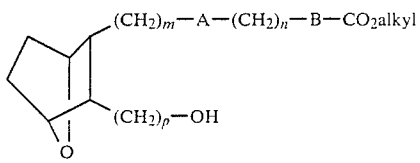

XLII by reacting XLI with sodium borohydride in a neutral solvent like methanol, ethanol or tetrahydrofuran. The alcohol XXXVIII may then be subjected to an etherification reaction with B, B' or B'' or to a thioetherification reaction with F to form the compounds of the invention.

Compounds of formula I wherein $R^1$ is aryl such as phenyl or substituted phenyl may also be prepared by reacting the alcohol XII, XVIII, XXVI, XXVII, XXVIII, XXXIII or XXXIIIA, with triphenylphosphine and diethylazodicarboxylate in solution with an inert solvent such as THF, and thereafter without isolating any products, reacting the above reaction mixture with an aryl alcohol wherein the hydroxy group is directly attached to the aromatic ring, such as phenol or a substituted phenol, under an inert atmosphere, such as argon or nitrogen, to form the ester of the structure

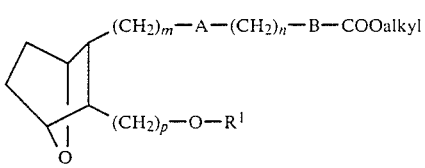

XLIII wherein $R^1$ is phenyl or substituted phenyl.

The esters within the scope of formula I (that is, where R is alkyl) can be converted to the free acid, that is, to IE

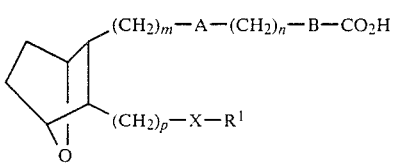

IE by treating the esters with an alkali metal hydroxide, such as lithium or sodium hydroxide to form the corresponding alkali metal salt (wherein R is an alkali metal such as Na, Li or K) followed by neutralization with an acid, such as dilute hydrochloric acid or oxalic acid to form the acid IA.

In another method for forming compounds of the invention wherein B is —CH=CH—, the 7-oxabicycloheptane ether of the structure XLIV

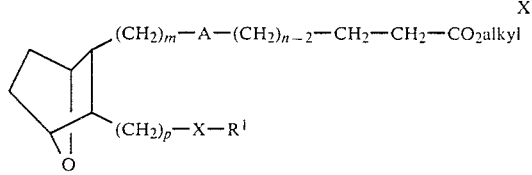

XLIV is subjected to phenylselenylation by reacting XLIV with lithium diisopropylamide at reduced temperatures of from about $-78°$ C. to about $0°$ C. in the presence of an inert organic solvent such as tetrahydrofuran, dimethoxyethane or ether; thereafter a solution of diphenyldiselenide in an inert organic solvent as described above is added and the reaction is maintained at reduced temperatures as described above to form the selenophenyl ester XLV.

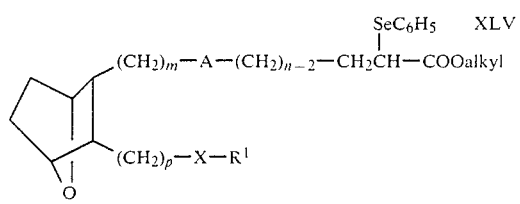

XLV

The selenophenyl ester XLV is next hydrolyzed by reaction with a strong base such as LiOH, $K_2CO_3$ or NaOH and then treated with strong acid such as HCl as described hereinbefore to form acid XLVI

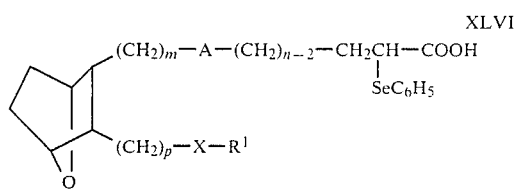

XLVI

The selenophenyl acid XLVI is then made to undergo a selenoxide elimination reaction wherein the selenophenyl acid is treated with hydrogen peroxide in an inert organic solvent such as tetrahydrofuran to form acid XLVII

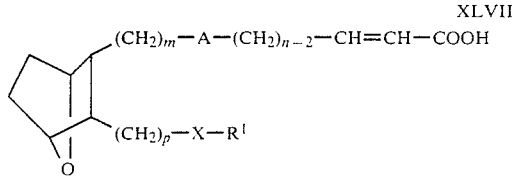

XLVII

To form compounds of formula I wherein X is

the sulfide derivative of formula I wherein X is S and A is O is subjected to an oxidation reaction, for example, by reacting same with sodium periodate, in the presence of methanol and tetrahydrofuran, to form the corresponding sulfinyl derivative

and sulfonyl derivative

Where A is S and X is S, oxidation of S in the lower side chain will cause similar oxidation of S in the upper side chain. The sulfinyl and sulfonyl derivatives may be separated by chromatography or other conventional separation procedures.

The tris(hydroxymethyl)aminomethane salt of any of the acids of formula I of the present invention is formed by reacting a solution of such acid in an inert solvent such as methanol with tris(hydroxymethyl)aminomethane and thereafter the solvent is removed by evaporation to leave the desired salt.

The compounds of this invention have four centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared as shown in the working Examples which follow and by employing starting materials and following the procedures as outlined in U.S. Pat. No. 4,143,054. Examples of such stereoisomers are set out below.

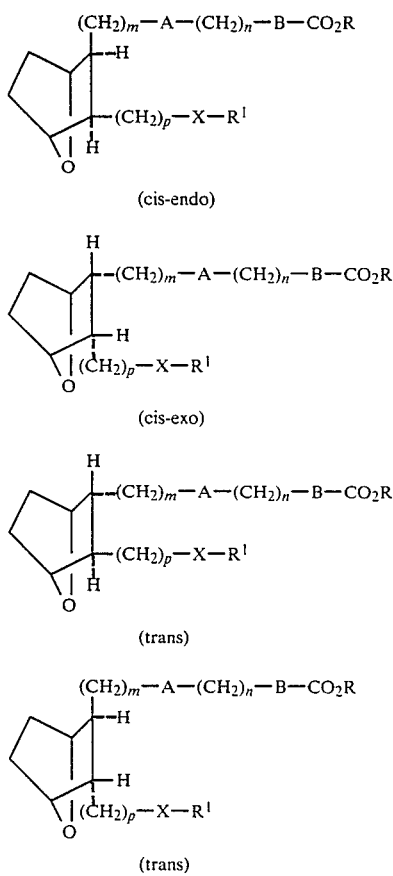

The nucleus in each of the compounds of the invention is depicted as

for matter of convenience; it will also be appreciated that the nucleus in the compounds of the invention may be depicted as

The compounds of this invention are cardiovascular agents useful as platelet aggregation inhibitors, such as inhibiting arachidonic acid-induced platelet aggregation (e.g., for treatment of thrombolytic disease, such as coronary or cerebral thromboses) and in inhibiting bronchoconstriction as induced by asthma. They are also selective thromboxane $A_2$ receptor antagonists and synthetase inhibitors, e.g., having a vasodilatory effect for treatment of myocardial ischemic disease, such as angina pectoris. The compounds of the invention are also arachidonic acid cyclooxygenase inhibitors. In addition, the compounds of the invention are useful as analgesic agents in the manner of aspirin and indomethacin as indicated by reaction thresholds to pressure in edematous hindpaws [Ref: Winter et al, J. Pharmacol, Exp. Ther. 150:165, 1965] and as antiinflammatory agents in mammals, as indicated by carrageenin-induced edema in the rat [Ref: Winter et al., J. Pharmacol., Exp. Ther. 141:369, 1963]. They may be used to decrease joint swelling, tenderness, pain and stiffness in conditions such as rheumatoid arthritis.

The compounds of the invention can be administered orally or parenterally to various mammalian species known to be subject to such maladies, e.g., cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The compounds of the invention may also be administered topically to any of the above mammalian species in amounts of from about 0.1 to 10 mg/kg in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following Examples represent preferred embodiments of the invention. Unless otherwise indicated, all temperatures are expressed in °C.

EXAMPLE 1

(1α,2β,3β,4α)-5-[[3-[(Hexyloxy)methyl]-7-oxabicyclo[2.2.1]hept-2-yl]methoxy]pentanoic acid, hexyl ester

A.
(1α,2β,3β,4α)-Cis-exo-7-oxabicyclo[2.2.1]heptane-2,3-dimethanol

To a suspension of 11.4 g lithium aluminum hydride (300 mmole, 1.6 eq) in 400 ml of dry THF at 0° C. was added dropwise a solution of 32 g cis-exo 7-oxabicyclo[2.2.1]heptane-2,3-dicarboxylic anhydride (190 mmole) in 400 ml of dry THF over a period of 1 hour. The reaction mixture was stirred at 25° C. for 18 hours, cooled to 0° C. and quenched by slow addition of a saturated $Na_2SO_4$ solution, and filtered. The solid was washed with three 100 ml portions of $CH_2Cl_2$. The combined organic layer was dried over $MgSO_4$ and concentrated to give 32 g of title diol as a colorless solid.

B.
(1α,2β,3β,4α)-Cis-exo-2-hydroxymethyl-3-benzyloxymethyl-7-oxabicyclo[2.2.1]heptane To a suspension of 3.08 g of sodium hydride (70 mmole, 1.1 eq., 50% oil dispersion), washed with ether, in 100 ml of dry DMF was added with stirring at 0° C. a solution of 10.0 g title A diol (64 mmole) in 30 ml of DMF over a period of 15 minutes. The mixture was stirred for 30 minutes at 0° C., 20 minutes at 25° C., cooled to 0° C. then 12.0 g of benzyl bromide (70 mmole, 1.1 eq) was added dropwise. After stirring at 25° C. for 2 hours, the reaction was quenched with an aqueous ammonium chloride solution, extracted with ether, dried over anhydrous $MgSO_4$ and concentrated. Purification was done on a silica gel column, eluting with 10–20% ethyl acetate in hexane to give 11.8 g of the title monobenzylether.

C.
(1α,2β,3β,4α)-5-[[3-Benzyloxymethyl-7-oxabicyclo[2.2.1]hept-2-yl]methoxy]pentanol, t-butyldimethylsilyl ether To a mixture of 6.73 g powdered potassium hydroxide (121 mmole, 10 eq.) in 20 ml of dry xylene was added a solution of 3.0 g of title B alcohol (12.1 mmole) in 10 ml of xylene. The mixture was heated to reflux and 15 ml of xylene was distilled off.

To the cooled remaining solution was added a solution of 6.18 g of 5-tert-butyldimethylsilyloxy n-pentyl mesylate in 10 ml of xylene. The resulting mixture was refluxed for 1 hour, cooled to 25° C. and diluted with 300 ml of ether. The ethereal solution was washed with two 50 ml portions of water, dried over anhydrous $MgSO_4$ and concentrated.

The residue was purified on a silica gel column, eluting with 20% ether in hexane to give 4.0 g of title compound as a yellow oil.

D.
(1α,2β,3β,4α)-5-[[3-Benzyloxymethyl-7-oxabicyclo[2.2.1]hept-2-yl]methoxy]pentanol To 536.5 mg of title C compound (1.19 mmole) in 2 ml of THF at 0° C. was added 755.4 mg of tetra-n-butylammonium fluoride. The mixture was stirred for 0° C. for 2 hours and at 25° C. for 1 hour, then diluted with 50 ml of ether. The ethereal solution was washed with two 10 ml portions of $H_2O$, 10 ml of brine, dried over anhydrous $MgSO_4$ and concentrated to give crude title alcohol as an oil. This was used without further purification.

E.
(1α,2β,3β,4α)-5-[[3-Benzyloxymethyl-7-oxabicyclo[2.2.1]hept-2-yl]methoxy]pentanoic acid, and

F.
(1α,2β,3β,4α)-5-[[3Benzyloxymethyl-7-oxabicyclo[2.2.1]hept-2-yl]methoxy]pentanoic acid, methyl ester To crude title D alcohol in 10 ml of acetone at 0° C. was added dropwise a solution of 2.67M Jones reagent until the reaction mixture remained orange. The mixture was stirred for an additional 30 minutes at 0° C. then quenched with isopropanol and diluted with 200 ml of ether. Anhydrous sodium acetate along with anhydrous magnesium sulfate were added. The mixture was stirred for 15 minutes at 25° C. and filtered through a bed of florosil. The filtrate was concentrated and the residue was treated with 100 ml of saturated $NaHCO_3$ solution and extracted with two 50 ml portions of ether. The aqueous layer was acidified with concentrated HCl, saturated with solid NaCl and extracted with five 50 ml portions of $CH_2Cl_2$, dried over anhydrous $MgSO_4$ and concentrated to give 260 mg of title E acid, as an oil.

The above acid, dissolved in 10 ml of ether, was treated with an ethereal solution of diazomethane to give 260 mg of title F ester.

G.
(1α,2β,3β,4α)-5-[[3-Hydroxymethyl-7-oxabicyclo[2.2.1]hept-2-yl]methoxy]pentanoic acid, methyl ester A mixture of 260 ml title F ester (0.71 mmole) and 130 mg of 10% palladium over carbon in 5 ml of ethylacetate was shaken in a Parr bottle under 40 lbs of hydrogen pressure, at 25° C. for 18 hours. The reaction mix was filtered through a bed of Celite and the filtrate was concentratred to give 200 mg of title G alcohol as an oil.

H.
(1α,2β,3β,4α)-5-[[3-[(Hexyloxy)methyl]-7-oxabicyclo[2.2.1]hept-2-yl]methoxy]pentanoic acid, hexyl ester To a solution of 504 mg of powdered potassium hydroxide (8.4 mmole, 10 eq.) in 40 ml of dry xylene was added a solution of 217 mg of title G alcohol (0.84 mmole) in 40 ml of xylene. The mixture was heated to reflux and 40 ml of xylene was distilled off. To the cooled remaining solution was added 1.5 g of hexyl mesylate (8.4 mmole, 10 eq.). The mixture was refluxed for 3 hours then cooled to 25° C., diluted with 200 ml of ether and washed with two 50 ml portions of $H_2O$. The organic layer was dried over anhydrous $MgSO_4$ and concentrated. The residue was purified on a silica gel column, eluting with 20% EtOAc/hexanes to give 200 mg of title oil (contaminated with some hexyl mesylate).

EXAMPLE 2

(1α,2β,3β,4α)-5-[[3-[(Hexyloxy)methyl]-7-oxabicyclo[2.2.1]hept-2-yl]methoxy]pentanoic acid To 200 mg of crude Example 1 compound (ca. 0.46 mmole) in 80 ml of THF and 20 ml of $H_2O$ at 0° C. was added 4.6 ml of 1M lithium hydroxide solution. The mixture was stirred at 25° C. for 20 hours then concentrated. The residue was diluted with 10 ml of H$_2$O and acidified with a saturated aqueous oxalic acid solution to pH 3. The aqueous solution was extracted with three 40 ml portions of ether. The combined organic layer was washed with two 40 ml portions of H$_2$O, dried over anhydrous MgSO$_4$ and concentrated. The residue was purified on a CC-7 silica gel column, eluting with a gradient of pentane/ether. The product was kept under high vacuum for five days to yield 155 mg of title compound as a clear oil.

TLC: silica gel; 7% MeOH/CH$_2$Cl$_2$; R$_f$~0.4.

Anal Calcd for C$_{19}$H$_{34}$O$_5$: C, 66.63; H, 10.00; Found: C, 66.75; H, 9.82

EXAMPLE 3

(1α,2β,3β,4α)-5-[[[3-[(Hexyloxy)methyl]-7-oxabicyclo[2.2.1]hept-2-yl]methyl]thio]pentanoic acid, hexyl ester

A.

(1α,2β,3β,4α)-cis-exo-[[3-Isopropyloxycarbonyloxymethyl-7-oxabicyclo[2.2.1]hept-2-yl]methyl]thioacetate To a solution of 10.5 g of triphenylphosphine (40 mmole, 2 eq.) in 100 ml of dry THF at 0° C. was added dropwise 8.5 g of 95% pure diisopropylazodicarboxylate (60 mmole, 2 eq.) over a period of 15 minutes. After stirring for 30 minutes, a solution of 4.88 g of Example 9 title A alcohol carbonate (20 mmole) and 1.43 ml of distilled thiol acetic acid (40 mmole, 2 eq.) in 10 ml of dry THF was added dropwise over a period of 20 minutes. The mixture was stirred at 0° C. for 30 minutes and at 25° C. for 1 hour, and then concentrated. The residue was triturated with ether/hexane, and then filtered. The filtrate was concentrated and purified on a silica gel column, eluting with 5% ethyl acetate in hexane followed by 10% ethyl acetate in hexane to give 5.12 g of title thioacetate as a colorless crystalline solid.

B.

(1α,2β,3β,4α)-cis-exo-[3-Hydroxymethyl-7-oxabicyclo[2.2.1]hept-2-yl]methanethiol To a slurry of 400 mg of 95% pure lithium aluminum hydride (13 mmole, 4.2 eq.) in 25 ml of dry THF at 0° C. under an argon atomsphere was added dropwise a solution of 1.9 g of title A thioacetate (6 mmole) in 100 ml of dry THF. The mixture was stirred at 0° C. for 30 minutes and at 25° C. for 1 hour and then quenched with a saturated sodium sulfate solution. The mixture was dried with anhydrous MgSO$_4$ and filtered. The filtrate was concentrated to give the crude title thio-alcohol as an oil.

This oil was used in the next step without purification.

C.

(1α,2β,3β,4α)-5-[[[3-Hydroxymethyl-7-oxabicyclo[2.2.1]hept-2-yl]methyl]thio]pentanoic acid, methyl and ethyl esters To a slurry of 480 mg of 50% sodium hydride in mineral oil (10 mmole, 2.1 eq.) in 20 ml of dry THF at 0° C. was added dropwise a solution of 820 mg of title B thioalcohol (4.71 mmole) in 5 ml of dry THF. After stirring for 20 minutes at 0° C., a solution of 3.17 ml of ethyl-5-bromovalerate (20 mmole, 4.2 eq.) was added dropwise. The reaction mixture was stirred at 0° C. for 2 hours and then quenched with a saturated solution of ammonium chloride. The layers were separated. The aqueous layer was acidified with a 2N HCl solution and extracted several times with CH$_2$Cl$_2$. The combined organic layer was dried over anhydrous MgSO$_4$ and concentrated. The residue was diluted with 25 ml of ether and treated with an etheral solution of diazomethane.

Purification was done on a silica gel column, eluting with 10% EtOAc/hexane followed by 20% EtOAc/hexane to give 540 mg of a mixture of title methyl and ethyl ester as a colorless oil.

D.

(1α,2β,3β,4α)-5-[[[3-[(Hexyloxy)methyl]-7-oxabicyclo[2.2.1]hept-2-yl]methyl]thio]pentanoic acid, hexyl ester To a solution of 583 mg of powdered potassium hydroxide (9.7 mmole, 10 eq.) in 50 ml of dry xylene was added a solution of 266.5 mg of title C alcohol (0.97 mmole) in 50 ml of dry xylene. The mixture was heated to reflux and 50 ml of xylene was distilled off. To the cooled remaining solution was added 1.7 g of hexyl mesylate (9.7 mmole, 10 eq.). The mixture was refluxed for 5 hours then cooled to 25° C., diluted with 200 ml of ether and washed with two 50 ml portions of H$_2$O. The organic layer was dried over anhydrous MgSO$_4$ and concentrated. The residue was purified on a silica gel column, eluting with 20% EtOAc/hexanes to give 200 mg of title oil (contaminated with a small amount of hexyl mesylate).

EXAMPLE 4

(1α,2β,3β,4α)-5-[[[3-[(Hexyloxy)methyl]-7-oxabicyclo[2.2.1]hept-2-yl]methyl]thio]pentanoic acid To 200 mg of crude Example 3 compound (ca. 0.45 mmole) in 80 ml of THF and 20 ml of H$_2$O saturated with argon at 0° C. was added 4.5 ml of a 1M lithium hydroxide solution. The mixture was stirred at 25° C. for 20 hours then concentrated. The residue was diluted with 10 ml of H$_2$O and acidified to pH 3 with a saturated aqueous solution of oxalic acid. The aqueous solution was extracted with three 40 ml portions of ether. The combined organic layer was washed with two 40 ml portions of H$_2$O, dried over anhydrous MgSO$_4$ and with two 40 ml portions of H$_2$O, dried over anhydrous MgSO$_4$ and concentrated. The residue was purified on a CC-7 silica gel column, eluting with a gradient of pentane/ether. The product was kept under high vacuum for 5 days to yield 148 mg of title compound as a white solid.

TLC: silica gel; 7% MeOH/CH$_2$Cl$_2$; R$_5$~0.55.

Anal Calcd for C$_{19}$H$_{34}$O$_4$S: C, 63.64; H, 9.56; S, 8.94; Found: C, 63.41; H, 9.52; S, 8.70

EXAMPLE 5

(1α,2β,3β,4α)-5-[[3-[(Hexylthio)methyl]-7-oxabicyclo[2.2.1]hept-2-yl]methoxy]pentanoic acid, hexyl ester

A.

(1α,2β,3β,4α)-5-[[3-(p-Toluenesulfonyloxymethyl)-7-oxabicyclo[2.2.1]hept-2-yl]methoxy]pentanoic acid, methyl ester To a solution of 544 mg (2.0 mmol) of (1α,2β,3β,4α)-5-[[3-hydroxymethyl-7-oxabicyclo[2.2.1]hept-2-yl]methoxy]pentanoic acid, methyl ester, prepared as described in Example 1 Part G, in 4 ml of dry pyridine is added 420 mg (2.2 mmol) of tosyl chloride. The mixture is stirred at room temperature under an argon atmosphere for 10 hours. The reaction mixture is diluted with 300 ml of ether, and washed with 1N aqueous HCl solution (3×100 ml). The ether layer is dried over anhydrous magnesium sulfate and concentrated in vacuo. Purification is effected by flash chromatography on 30 g of silica gel 60 using 50% hexane in ether as eluant to give 615 mg of title compound.

B.

(1α,2β,3β,4α)-5-[[3-[(Hexylthio)methyl]-7-oxabicyclo[2.2.1]hept-2-yl]methoxy]pentanoic acid, hexyl ester To a solution of 132 mg (1.17 mmol) of potassium t-butoxide in 10 ml of dry THF under argon is added 378 mg (3.21 mmol) of 1-hexanethiol. To this mixture is added a solution of 425 mg (1.0 mmol) of Part A tosylate in 5 ml of THF. The reaction mixture is stirred at room temperature under argon for 2.5 hours and then heated to reflux for 5.5 hours. The cooled reaction is diluted with 300 ml of ether and poured into 100 ml of saturated NaHCO$_3$ solution. The aqueous layer is extracted with ether (2×100 ml). The combined ether extracts (500 ml) are washed with 0.5N aqueous sodium hydroxide (2×100 ml), brine (100 ml), and then dried (MgSO$_4$), filtered and concentrated in vacuo to give 675 g of crude oil. Purification is effected by chromatography on 25.2 g of silica gel 60 using 5:1 pet ether:ether as eluant to give 300 mg of title product as an oil.

EXAMPLE 6

(1α,2β,3β,4α)-5-[[3-[(Hexylthio)methyl]-7-oxabicyclo[2.2.1]hept-2-yl]methoxy]pentanoic acid Following the procedure of Example 2 except substituting the Example 5 ester for the Example 1 ester, the title compound is obtained.

EXAMPLE 7

(1α,2β,3β,4α)-5-[[[3-[(Hexylthio)methyl]-7-oxabicyclo[2.2.1]hept-2-yl]methyl]thio]pentanoic acid, hexyl ester

A.

(1α,2β,3β,4α)-5-[[3-(p-Toluenesulfonyloxymethyl)-7-oxabicyclo[2.2.1]-hept-2-yl]methyl]thio]pentanoic acid, methyl ester To a solution of 576 mg (2.0 mmol) of (1α,2β,3β,4α)-5-[[[3-hydroxymethyl-7-oxabicyclo[2.2.1]hept-2-yl]methyl]thio]pentanoic acid, methyl and ethyl esters prepared as described in Example 3 Part C in 4 ml of dry pyridine is added 420 mg (2.2 mmol) of tosyl chloride. The mixture is stirred at room temperature under an argon atmosphere for 10 hours. The reaction mixture is diluted with 300 ml of ether, washed with 1N aqueous HCl solution (3×100 ml), and 0.5N aqueous NaOH solution (3×100 ml). The ether layer is dried over anhydrous magnesium sulfate and concentrated in vacuo. Purification is effected by flash chromatography on 30 g of silica gel 60 using 50% hexane in ether as eluant to give 860 mg of title compound.

B.

(1α,2β,3β,4α)-5-[[[3-[(Hexylthio)methyl]-7-oxabicyclo[2.2.1]hept-2-yl]methyl]thio]pentanoic acid, hexyl ester To a solution of 132 mg (1.17 mmol) of potassium t-butoxide in 10 ml of dry THF under argon is added 378 mg (3.21 mmol) of 1-hexanethiol. To this mixture is added a solution of 442 mg (1.0 mmol) of Part A tosylate in 5 ml of THF. The reaction mixture is stirred at room temperature under argon for 2.5 hours and then heated to reflux for 5.5 hours. The cooled reaction is diluted with 300 ml of ether and poured into 100 ml of saturated NaHCO$_3$ solution. The aqueous layer is extracted with ether (2×100 ml). The combined ether extracts (500 ml) are washed with 0.5N aqueous sodium hydroxide (2×100 ml), brine (100 ml), and then dried (MgSO$_4$), filtered and concentrated in vacuo to give 690 g of crude oil. Purification is effected by chromatography on 25.2 g of silica gel 60 using 5:1 pet ether:ether as eluant to give 310 mg of title product as an oil.

EXAMPLE 8

(1α,2β,3β,4α)-5-[[[3-[(Hexylthio)methyl]-7-oxabicyclo[2.2.1]hept-2-yl]methyl]thio]pentanoic acid Following the procedure of Example 4 except substituting the Example 7 ester for the Example 3 ester, the title compound is obtained.

EXAMPLE 9

(1α,2β,3β,4α)-5-[[[3-[(Hexyloxy)methyl]-7-oxabicyclo[2.2.1]hept-2-yl]ethyl]thio]pentanoic acid, hexyl ester

A.

(1α,2β,3β,4α)-cis-exo-3-Isopropyloxycarbonyloxymethyl-2-hydroxymethyl-7-oxabicyclo[2.2.1]heptane To a suspension of 11.4 g of lithium aluminum hydride (300 mmole, 1.6 eq) in 400 ml of dry THF at 0° C. was added dropwise a solution of 32 g (1α,2β,3β,4α)-cis-exo-[7-oxabicyclo[2.2.1]hept-2-ylα-2,3-dicarboxylic acid anhydride (mesoanhydride) (190 mmole) in 400 ml of dry THF over a period of 1 hour. The reaction mixture was stirred at 25° C. for 18 hours, cooled to 0° C. and quenched by slow addition of a saturated Na$_2$SO$_4$ solution, and filtered. The solid was washed with three 100 ml portions of CH$_2$Cl$_2$. The combined organic layer was dried over MgSO$_4$ and concentrated to give 32 g of (1α,2β,3β,4α)-cis-exo-7-oxabicyclo[2.2.1]heptane-2,3-dimethanol (meso-diol) as a colorless solid.

To a solution of 10 g (63.2 mmole) of meso-diol in 40 ml dry THF at 0° C. was added with stirring 55 ml of a 12.5% by weight solution of phosgene in toluene (63.2 mmole, 1 eq.) dropwise over a period of 30 minutes. Argon was then bubbled through the reaction mixture for 15 minutes. The mixture was concentrated to give a crude oil of (1α,2β,3β,4α)-cis-exo-3-chlorocarbonyloxy-2-hydroxymethyl-7-oxabicyclo[2.2.1]heptane.

This oil was dissolved in 30 ml of dry CH$_2$Cl$_2$ and cooled to −50° C. To this solution was added dropwise a solution of 10 ml pyridine in 10 ml CH$_2$Cl$_2$. It was stirred for 10 minutes and quenched with H$_2$O. The mixture was extracted thoroughly with CH$_2$Cl$_2$. The organic extract was dried over MgSO$_4$ and concentrated to give (1α,2β,3β,4α)-7-oxabicyclo[2.2.1]heptane 2,3-dimethanol carbonate (cyclic carbonate) as a crystalline solid (10.7 g).

A mixture of 10.7 g of (1α,2β,3β,4α)-cis-exo-7-oxabicyclo[2.2.1]heptane 2,3-dimethanol carbonate (cyclic carbonate) (58.1 mmole) in 100 ml isopropanol was refluxed for 24 hours. Excess isopropanol was removed under reduced pressure to give 14.4 g title A compound (hydroxycarbonate) as a viscous oil.

B.

(1α,2β,3β,4α)-cis-exo-3-Isopropyloxycarbonyloxymethyl-2-p-toluenesulfonyloxymethyl-7-oxabicyclo[2.2.1]heptane To a solution of 19.7 g of title A alcohol (80 mmole) in 30 ml $CH_2Cl_2$ and 12.8 ml pyridine (160 mmole, 2 eq.) was added 18.5 g p-toluenesulfonyl chloride (96 mmole, 1.2 eq.). The mixture was stirred at 25° C. for 36 hours then diluted with 200 ml ether, and washed with 100 ml brine.

The organic layer was dried over $MgSO_4$ and concentrated to give 32.8 g of title crude tosylate as an oil.

C.

(1α,2β,3β,4α)-cis-exo-3-Isopropyloxycarbonyloxymethyl-2-cyanomethyl-7-oxabicyclo[2.2.1]heptane To a solution of 24.0 title B crude tosylate (60 mmole) in 20 ml DMSO was added with stirring 6.0 g powdered sodium cyanide (120 mmole, 2 eq.). The mixture was heated at 90°–95° C. for 1.5 hours under an argon atmosphere. The cooled mixture was diluted with 50 ml water and extracted with five 100 ml portions of ether. The ethereal extracts were dried over anhydrous $MgSO_4$ and filtered though a bed of Florosil ®. The filtrate was concentrated, and the residue was recrystallized with ether/hexanes to give 8.4 g of title cyanocarbonate as a light yellow crystalline solid.

D.

(1α,2β,3β,4α)-cis-exo-3-Hydroxymethyl-2-cyanomethyl-7-oxabicyclo[2.2.1]heptane

To 8.4 g of title C cyanocarbonate (33.2 mmole) was added 75 ml of a 1% solution of potassium carbonate in methanol-water (2:1). The reaction mixture was stirred at 25° C. for 6 hours, then acidified with 2N HCl solution, saturated with sodium chloride and extracted with six 100 ml portions of $CH_2Cl_2$. The combined organic layer was dried over anhydrous $MgSO_4$ and concentrated to give 5.5 g of crude title cyanoalcohol as a light yellow oil.

E.

(1α,2β,3β,4α)-cis-exo-3-t-Butyldimethylsilyloxymethyl-2-cyanomethyl-7-oxabicyclo[2.2.1]heptane To a solution of 5.0 g title D alcohol (30 mmole) in 50 ml of dry $CH_2Cl_2$ and 10 ml of triethylamine (70 mmole, 3.3 eq.) at 0° C. was added with stirring 490 mg 4-dimethylaminopyridine (4 mmole) and 5.28 g t-butyldimethylsilyl chloride (35 mmole, 1.16 eq.). The reaction mixture was slowly warmed to 25° C. and stirred for 18 hours, then diluted with 200 ml ether and filtered through a small bed of anhydrous $MgSO_4$. The filtrate was concentrated. Purification was done on a silica gel column, eluting with 15% ethyl acetate/hexanes to give 10.25 g of title silyl ether as a light yellow oil.

F.

(1α,2β,3β,4α)-cis-exo-3-t-Butyldimethylsilyloxymethyl-2-formylmethyl-7-oxabicyclo[2.2.1]heptane To a solution of 10.0 g of title E silyl ether (26.2 mmole) in 30 ml of dry toluene at −78° C. under an argon atmosphere was added dropwise 25 ml of a 25% by weight solution of diisobutylaluminum hydride (44 mmole, 1.6 eq.) in toluene. The mixture was stirred at −78° C. for 4 hours, quenched at −78° C. with a saturated solution of ammonium chloride, warmed to 0° C. and acidified with 1N HCl solution, extracted with three 100 ml portions of $CH_2Cl_2$, dried over anhydrous $MgSO_4$ and concentrated to give 9.3 g of crude title aldehyde.

G.

(1α,2β,3β,4α)-cis-exo-2-[3-t-Butyldimethylsilyloxymethyl-7-oxabicyclo[2.2.1]hept-2-yl]ethanol To 9.3 g crude title F aldehyde (32.7 mmole) in 30 ml of dry THF at 0° C. under an argon atmosphere was added portionwise 1.0 g lithium aluminum hydride (26.0 mmole, 3.2 eq.) with stirring. The reaction mixture was stirred while being warmed to 25° C. over a period of 1 hour, quenched by slow addition of a saturated sodium sulfate at 0° C., dried over anhydrous $MgSO_4$ and filtered. The solid was washed with $CH_2Cl_2$. The combined filtrate was concentrated to give a crude oil. This oil was purified on a silica gel column, eluting with 30% EtOAc/hexanes to give 8.55 g title alcohol as a colorless oil.

H.

(1α,2β,3β,4α)-2-[2-[3-t-Butyldimethylsilyloxymethyl-7-oxabicyclo[2.2.1]hept-2-yl]ethyl]thioacetate To a solution of 5.25 g triphenylphosphine (20 mmole, 2 eq.) in 60 ml dry THF at 0° C. was added dropwise 4.16 g diisopropylazodicarboxylate (20 mmole, 2 eq.) over a period of 15 minutes. The mixture was stirred at 0° C. for 30 minutes then to it was added dropwise a solution of 2.6 g title G alcohol (10 mmole) and 1.45 ml of thiolacetic acid (20 mmole, 2 eq.) in 10 ml dry THF. The reaction mixture was stirred at 0° C. for 1 hour and 25° C. for 3 hours, then concentrated. The residue was triturated with ether/hexane, filtered, and the filtrate was concentrated and purified on a silica gel column, eluting with 10% EtOAc/hexanes to give 2.3 g title thioacetate as a light yellow oil.

I.

(1α,2β,3β,4α)-2-[2-[3-Hydroxymethyl-7-oxabicyclo[2.2.1]hept-2-yl]ethyl]thioacetate To a solution of 2.3 g title H thioacetate (6.7 mmole) in 20 ml dry THF at 0° C. was added 2.23 g tetra-n-butylammoniumfluoride trihydrate (7.07 mmole, 1.05 eq.) in 5 ml dry THF. The reaction mixture was warmed at 25° C. and stirred for 18 hours, diluted with 100 ml ether and washed with 30 ml saturated $NaHCO_3$ solution, dried over anhydrous $MgSO_4$ and concentrated to give a crude oil.

Purification was done on a silica gel column, eluting with 20% EtOAc/hexanes then 50% EtOAc/hexanes to give 1.22 g title alcohol thioacetate as a colorless oil.

J.

(1α,2β,3β,4α)-2-[3-Hydroxymethyl-7-oxabicyclo[2.2.1]hept-2-yl]ethanethiol

To a slurry of 200 mg lithium aluminum hydride (5.27 mmole, 4 eq.) in 20 ml dry THF at 0° C. was added a solution of 1.22 g title I thioacetate (5.3 mmole) in 5 ml THF dropwise under an argon atmosphere. The reaction mixture was stirred at 0° C. for 1 hour, then quenched with a saturated sodium sulfate solution, dried with anhydrous $MgSO_4$, then filtered. The filtrate was concentrated to give 900 mg title thiol as a colorless oil.

K.
[1α,2β(5E),3β,4α]-5-[[2-[3-Hydroxymethyl-7-oxabicyclo[2.2.1]hept-2-yl]ethyl]thio]pentanoic acid, ethyl ester To a slurry of 1.38 g of dried and powdered sodium hydride (5.75 mmole, 1.2 eq.) in 20 ml dry tetrahydrofuran at 0° C. is added a solution of 900 mg title J thiol (4.8 mmole) in 5 ml THF followed by 1.75 ml of ethyl-5-bromovalerate (11.05 mmole, 2.3 eq.). The reaction mixture is stirred at 0° C. for 10 hours, then diluted with 100 ml ether and filtered through a pad of anhydrous MgSO$_4$. The filtrate was concentrated. The residue is purified on a silica gel column, eluting with 20% EtOAc/hexanes and 50% EtOAc/hexanes to give 1.22 g of title alcohol as a colorless oil.

L.
(1α,2β,3β,4α)-5-[[2-[3-[(Hexyloxy)methyl]-7-oxabicyclo[2.2.1]hept-2-yl]ethyl]thio]pentanoic acid, hexyl ester Following the procedure of Example 3 Part D except substituting the above Part K alcohol for the Example 3 Part C alcohol, the title compound is obtained.

EXAMPLE 10
(1α,2β,3β,4α)-5-[2-[3-[(Hexyloxy)methyl]-7-oxabicyclo[2.2.1]hept-2-yl]ethylthio]pentanoic acid Following the procedure of Example 9 except substituting the Example 5 hexyl ester for the Example 3 hexyl ester, the title compound is obtained.

EXAMPLE 11
(1α,2β,3β,4α)-4-[2-[3-[(Hexyloxy)methyl]-7-oxabicyclo[2.2.1]hept-2-yl]ethoxy]butanoic acid, hexyl ester

A.
(1α,2β,3β,4α)-3-Cyanomethyl-2-benzyloxymethyl-7-oxabicyclo[2.2.1]heptane

To a slurry of 1.1 g of sodium hydride (21 mmole, 50% oil dispersion in 25 ml of dry DMF at 0° C. was added a solution of 3.34 g of Example 9 Part D cyanoalcohol (20 mmole) in 10 ml of DMF over a period of 10 minutes, After stirring for an additional 15 minutes, 3.6 g of benzyl bromide was added dropwise. The reaction mixture was stirred for 30 minutes at 0° C. and 3 hours at 25° C. then quenched with a saturated ammonium chloride solution, and diluted with ether. The organic layer was washed with brine. The combined aqueous layer was re-extracted with ether. The combined organic layer was dried over anhydrous MgSO$_4$ and concentrated to leave an oil. The crude oil was chromatographed on a silica gel column, eluting with 10-20% ethyl acetate in hexanes to give 4.43 g of the title A benzyl ether.

B.
(1α,2β,3β,4α)-2-[3-Benzyloxymethyl-7-oxabicyclo[2.2.1]hept-2-yl]acetaldehyde and

C.
(1α,2β,3β,4α)-2-[3-Benzyloxymethyl-7-oxabicyclo[2.2.1]hept-2-yl]ethanol

To a solution of 4.43 g of title A nitrile (17.24 mmole) in 20 ml of dry toluene at −78° C. was added dropwise 20 ml of a 25% by weight solution of diisobutylaluminum hydride in toluene (35 mmole, 2 eq.). After stirring at −78° C. for 4 hours the reaction was quenched with a saturated ammonium chloride solution. The mixture was warmed to 25° C. and 50 ml of a 1N aqueous hydrochloric acid solution was added. The organic layer was separated and the aqueous layer was extracted several times with ether. The combined organic extract was dried over anhydrous MgSO$_4$ and concentrated to give 4.55 g of crude title B aldehyde.

To the above crude title B aldehyde (ca. 17.24 mmole) in 30 ml of dry THF at 0° C. was added 380 mg of 95% pure lithium aluminum hydride (10 mmole, 2.3 eq.) portionwise. After stirring while warming to 25° C. over a period of 1 hour, the reaction was quenched with a saturated sodium sulfate solution. Solid anhydrous MgSO$_4$ was added and the mixture was filtered. The filtrate was concentrated to give 4.25 g of title C alcohol as a colorless oil.

D.
(1α,2β,3β,4α)-4-[2-[3-Benzyloxymethyl-7-oxabicyclo[2.2.1]hept-2-yl]ethoxy]butanol, t-butyldimethylsilyl ether To a mixture of 4.5 g of powdered potassium hydroxide (82.6 mmole, 10 eq.) in 20 ml of dry xylene was added a solution of 2.0 g of title C alcohol (8.26 mmole) in 10 ml of xylene. The mixture was heated to reflux and 15 ml of xylene was distilled off.

To the cooled remaining solution was added a solution of 4.0 g of 4-tert-butyldimethylsilyloxy n-butylmesylate in 10 ml of xylene. The resulting mixture was refluxed for 1 hour, cooled to 25° C. and diluted with 300 ml of ether. The ethereal solution was washed with two 50 ml portions of water, dried over anhydrous MgSO$_4$ and concentrated. The residue was purified on a silica gel column, eluting with 20% ether in hexanes to give 1.4 g of title D compound as a yellow oil.

E.
(1α,2β,3β,4α)-4-[2-[3-Benzyloxymethyl-7-oxabicyclo[2.2.1]hept-2-yl]ethoxy]butanol To 1.2 g of title D compound (2.68 mmole) in 5 ml of THF at 0° C. was added 1.1 g of tetra-n-butylammonium fluoride (3.46 mmole, 1.3 eq.). The mixture was stirred at 0° C. for 1 hour and at 25° C. for 1 hour then diluted with 50 ml of ether. The ethereal solution was washed with two 10 ml portions of H$_2$O, 10 ml of brine, dried over anhydrous MgSO$_4$ and concentrated to give crude title E alcohol as an oil. This was used without purification.

F.
(1α,2β,3β,4α)-4-[2-[3-Benzyloxymethyl-7-oxabicyclo[2.2.1]hept-2-yl]ethoxy]butanoic acid and

G.
(1α,2β,3β,4α)-4-[2-[3-Benzyloxymethyl-7-oxabicyclo[2.2.1]hept-2-yl]ethoxy]butanoic acid, methyl ester To crude title E alcohol in 30 ml of acetone at 0° C. was added dropwise a solution of 2.6M Jones' reagent until the reaction mixture remained orange. The mixture was stirred for an additional 30 minutes at 0° C. then quenched with isopropanol and diluted with 200 ml of ether. Anhydrous sodium acetate along with anhydrous magnesium sulfate was added. The mixture was stirred for 15 minutes at 25° C. and filtered through a bed of Florosil®. The filtrates were concentrated. The residue was treated with 200 ml of saturated NaH- CO₃ solution and extracted with two 50 ml portions of ether. The aqueous layer was acidified with concentrated HCl, saturated with solid NaCl and extracted with five 100 ml portions of $CH_2Cl_2$, dried over anhydrous $MgSO_4$ and concentrated to give title F acid as an oil.

The above title F acid, dissolved in 30 ml of ether, was treated with an ethereal solution of diazomethane to give an oil which was purified on a silica gel column, eluting with 20% EtOAc in hexanes to yield 500 mg of pure title G ester.

H.
(1α,2β,3β,4α)-4-[2-[3-Hydroxymethyl-7-oxabicyclo[2.2.1]hept-2-yl]ethoxy]butanoic acid, methyl ester and

I.
(1α,2β,3β,4α)-4-[2-[3-Formyl-7-oxabicyclo[2.2.1]hept-2-yl]ethoxy]butanoic acid, methyl ester A mixture of 500 mg of title G ester (1.38 mmole), 250 mg of 10% palladium over carbon in 10 ml of ethyl acetate and 1 ml of glacial acetic acid was shaken in a Parr bottle under 40 lbs. of hydrogen pressure at 25° C. for 18 hours. The mixture was filtered through a bed of Celite and concentrated to give 242 mg of title H alcohol as an oil.

To 1.9 ml of pyridine (13.3 mmole, 15 eq.) in 20 ml of dry $CH_2Cl_2$ at 25° C. was added 1.3 g of chromium trioxide (13.3 mmole, 15 eq.). The mixture was stirred for 1 hour at 25° C. 2 g of Celite along with a solution of 242 mg of title H alcohol (0.89 mmole) in 5 ml of $CH_2Cl_2$ was added. After stirring for 30 minutes at 25° C., the reaction mixture was diluted with 100 ml of ether and filtered through a bed of Fluorosil ®. The filtrate was concentrated to yield 200 mg of title I aldehyde as an oil.

J.
(1α,2β,3β,4α)-4-[2-[3-[(Hexyloxy)methyl]-7-oxabicyclo[2.2.1]hept-2-yl]ethoxy]butanoic acid, hexyl ester Following the procedure of Example 1 Part H except substituting the above Part I alcohol for the Example 1 Part G alcohol, the title compound is obtained.

EXAMPLE 12

(1α,2β,3β,4α)-4-[2-[3-[(Hexyloxy)methyl]-7-oxabicyclo[2.2.1]hept-2-yl]ethoxy]butanoic acid Following the procedure of Example 2 except substituting the Example 11 hexyl ester for the Example 1 hexyl ester, the title compound is obtained.

EXAMPLE 13

(1α,2β,3β,4α)-5-[[2-[3-[(Hexylthio)methyl]-7-oxabicyclo[2.2.1]hept-2-yl]ethyl]thio]pentanoic acid Following the procedure of Example 7 except substituting [1α,2β(5E)3β,4α]-5-[[2-[3-hydroxymethyl-7-oxabicyclo[2.2.1]hept-2-yl]ethyl]thio]pentanoic acid, methyl and ethyl esters (prepared in Example 9, Part K) for the Example 3 Part C alcohol, the title compound is obtained.

EXAMPLE 14

(1α,2β,3β,4α)-4-[[2-[3-[(Hexylthio)methyl]-7-oxabicyclo[2.2.1]hept-2-yl]ethoxy]butanoic acid Following the procedure of Examples 5 and 6 except substituting (1α,2β,3β,4α)-4-[2-[3-hydroxymethyl-7-oxabicyclo[2.2.1]hept-2-yl]ethoxy]butanoic acid, methyl ester (prepared in Example 11, Part N) for the Example 1 Part G alcohol, the title compound is obtained.

EXAMPLE 15

(1α,2β,3β,4α)-5-[[3-[2-(Hexyloxy)ethyl]-7-oxabicyclo[2.2.1]hept-2-yl]methoxy]pentanoic acid

A.
(1α,2β,3β,4α)-5-[[3-Formyl-7-oxabicyclo[2.2.1]hept-2-yl]methoxy]pentanoic acid, methyl ester To 5.44 g of (1α,2β,3β,4α)-5-[[3-hydroxymethyl-7-oxabicyclo[2.2.1]hept-2-yl]methoxy]pentanoic acid, methyl ester prepared as described in Example 1, Part G (20 mmol) in 65 ml of dry $CH_2Cl_2$ at 25° C. is added 13.2 Celite, 1.7 g NaOAc (6.15 mmole, 30 mole %) and 12.94 g pyridinium chlorochromate (60 mmole, 3 eq.). The mixture is stirred at 25° C. for 2 hours then diluted with 1000 ml ether and filtered through a bed of Florosil ®. The filtrate is concentrated to give 5.25 g of title aldehyde as a clear oil which is used in the next reaction without further purification.

B.
(1α,2β,3β,4α)-5-[[3-(2-Oxo)ethyl]-7-oxabicyclo[2.2.1]hept-2-yl]methoxy]pentanoic acid, methyl ester Into a dry 100 ml round bottom 3-necked flask containing a stir bar is added dried 3.27 g (9.54 mmoles) methoxymethyltriphenylphosphonium chloride (($C_6H_5)_3P^+$—$CH_2OCH_3Cl^-$) and 30 ml distilled toluene (stored over molecular sieves). The resulting suspension is stirred in an ice-bath, under argon, until cold and then a 1.4M solution of 5.73 ml (8.01 mmol) of potassium t-amylate in toluene is added dropwise. A bright red solution formed which is stirred at 0° C. for an additional 35 minutes. Thereafter, a solution of 1.037 g (3.84 mmol) (1α,2β,3β,4α)-5-[[3-formyl-7-oxabicyclo[2.2.1]hept-2-yl]methoxy]pentanoic acid, methyl ester in 10 ml toluene is added by means of a dropping funnel over a 35 minute period with the ice-bath still in place. The reaction is then quenched by addition of 2.3 g (39 mmol) acetic acid in 5 ml ether. The reaction mixture is immediately poured into 200 ml saturated $NH_4Cl$, and extracted with ether (4×200 ml). The combined ether phases are washed with NaCl saturated solution, and dried ($MgSO_4$) and concentrated to yield an oil in a white crystalline solid (phosphine oxide). The white solid is triturated with EtOAc and the mother liquor is purified by chromatography on an LPS-1 silica column to obtain the enol-ether. The enol-ether is dissolved in 20 ml of THF and then treated with 10 ml of a 20% aqueous trifluoroacetic acid solution. After 1 hour at room temperature, trifluoroacetic acid is quenched by careful addition of sodium bicarbonate. The reaction mixture is then extracted several times with methylene chloride. The combined methylene chloride extract is dried over anhydrous magnesium sulfate and concentrated under reduced pressure. Chromatography on a LPS-1 silica gel column and elution with 15–30% ethylacetate in hexane gives 980 mg of title B aldehyde.

C.
(1α,2β,3β,4α)-5-[[3-(2-Hydroxyethyl)-7-oxabicyclo[2.2.1]hept-2-yl]methoxy]pentanoic acid ester The aldehyde (980 g, 3.45 mmol) from part B in methanol (50 ml) is treated with $NaBH_4$ (0.19 g, 5 mmol) in an argon atmosphere at 0° C. After stirring at 0° C. for 1 hour, the reaction is quenched by addition of 2N HCl (to pH 2). The methanol is removed in vacuo and the reaction mixture is taken up in ether. The ether solution is washed with saturated $KHCO_3$, saturated NaCl and dried ($MgSO_4$). The ether is evaporated to yield the title C compound.

D.

(1α,2β,3β,4α)-5-[[3-[2-(Hexyloxy)ethyl]-7-oxabicyclo[2.2.1]hept-2-yl]methoxy]pentanoic acid Following the procedure of Example 1, Part H and Example 2 except substituting the above part C alcohol for the Example 1 Part G alcohol used in Example 1 Part H, the title compound is obtained.

EXAMPLE 16

(1α,2β,3β,4α)-5-[[3-[2-(Hexyloxy)ethyl]-7-oxabicyclo[2.2.1]hept-2-yl]methyl]thio]pentanoic acid

A.

(1α,2β,3β,4α)-5-[[3-(2-Hydroxyethyl)-7-oxabicyclo[2.2.1]hept-2-yl]methyl]thio]pentanoic acid, methyl ester Following the procedure of Example 15 Parts A to C except substituting (1α,2β,3β,4α)-5-[[3-hydroxymethyl-7-oxabicyclo[2.2.1]hept-2-yl]methyl]thio]pentanoic acid, methyl and ethyl esters (prepared as described in Example 3, Part C) for the Example 1 Part G alcohol, the title compound is obtained.

B.

(1α,2β,3β,4α)-5-[[[3-[2-(Hexyloxy)ethyl]-7-oxabicyclo[2.2.1]hept-2-yl]methyl]thio]pentanoic acid Following the procedure of Examples 1 Part H and Example 2 except substituting the above Part A alcohol for the alcohol used in Example 1 Part H, the title compound is obtained.

EXAMPLE 17

(1α,2β,3β,4α)-5-[[3-[(2-Hexylthio)ethyl]-7-oxabicyclo[2.2.1]-hept-2-yl]methoxy]pentanoic acid Following the procedure of Examples 5 and 6 except substituting (1α,2β,3β,4α)-5-[[3-(2-hydroxyethyl)-7-oxabicyclo[2.2.1]-hept-2-yl]methoxy]pentanoic acid, methyl ester (prepared as described in Example 15 Part C) for the Example 1 Part G alcohol, the title compound is obtained.

EXAMPLE 18

(1α,2β,3β,4α)-5-[[[3-[2-(Hexylthio)ethyl]-7-oxabicyclo[2.2.1]hept-2-yl]methyl]thio]pentanoic acid

A.

(1α,2β,3β,4α)-5-[[[3-Formyl-7-oxabicyclo[2.2.1]hept-2-yl]methyl]thio]pentanoic acid, methyl ester To a solution of 4 ml of oxalyl chloride (35 mmole, 4 eq.) in 10 ml of dry methylene chloride at −60° C. is added dropwise 6.5 ml of dry dimethylsulfoxide (90 mmole, 10 eq.) over a period of 15 minutes. After stirring for an additional 30 minutes, a solution of 2.51 g of (1α,2β,3β,4α)-5-[[[3-hydroxymethyl-7-oxabicyclo[2.2.1]hept-2-yl]methyl]thio pentanoic acid, methyl ester, prepared as described in Example 3 Part C (8.7 mmole) in 10 ml of dry methylene chloride is added dropwise over a period of 15 minutes. The reaction mixture is stirred at −60° C. for 30 minutes and then 10 ml of distilled triethylamine (~70 mmole) is added. The reaction is then warmed to room temperature and water is added. It is then stirred at room temperature for additional 30 minutes, whereupon it is extracted with methylene chloride and washed with saturated bicarbonate solution. The organic layer is dried over anhydrous magnesium sulfate and concentrated under reduced pressure.

Purification of the crude residue on a LPS-1 silica gel column and elution with 10–30% ethyl acetate in hexane gives 1.72 g of title A aldehyde.

B.

(1α,2β,3β,4α)-5-[[[3-(2-Oxo)ethyl]-7-oxabicyclo[2.2.1]hept-2-yl]methyl]thio]pentanoic acid, methyl ester Into a dry 100 ml round bottom 3-necked flask containing a stir bar is added dried 3.27 g (9.54 mmoles) methoxymethyltriphenylphosphonium chloride ($(C_6H_5)_3P^+$—$CH_2OCH_3Cl^-$) and 30 ml distilled toluene (stored over molecular sieves). The resulting suspension is stirred in an ice-bath, under argon, until cold and then a 1.4M solution of 5.73 ml (8.01 mmol) of potassium t-amylate in toluene is added dropwise. A bright red solution forms which is stirred at 0° C. for an additional 35 minutes. Thereafter, a solution of 1.08 g (3.84 mmol) (1α,2β,3β,4α)-5-[[[3-formyl-7-oxabicyclo[2.2.1]hept-2-yl]methyl]thio]pentanoic acid, methyl ester in 10 ml toluene is added by means of a dropping funnel over a 35 minute period with the ice-bath still in place. The reaction is then quenched by addition of 2.3 g (39 mmol) acetic acid in 5 ml ether. The reaction mixture is immediately poured into 200 ml saturated $NH_4Cl$, and extracted with ether (4×200 ml). The combined ether phases are washed with NaCl saturated solution, and dried ($MgSO_4$) and concentrated to yield an oil in a white crystalline solid (phosphine oxide). The white solid is triturated with EtOAc and the mother liquor is purified by chromatography on an LSP-1 silica column to obtain the enol-ether. The enol ether is dissolved in 20 ml of THF and is then treated with 10 ml of a 20% aqueous trifluoro acetic acid solution. After 1 hour at room temperature, trifluoroacetic acid is quenched by addition of solid sodium bicarbonate. The reaction mixture is then extracted with methylene chloride. The methylene chloride extract is dried over anhydrous magnesium sulfate and concentrated under reduced pressure. Chromatography of the crude residue on a LPS-1 silica gel column and elution with 15–30% ethyl acetate in hexane gives 1.02 g of title B aldehyde.

C.

(1α,2β,3β,4α)-5-[[[3-(2-Hydroxyethyl)-7-oxabicyclo[2.2.1]hept-2-yl]methyl]thio]pentanoic acid methyl ester The aldehyde (1.02 g, 3.45 mmol) from part B in methanol (50 ml) is treated with $NaBH_4$ (0.19 g, 5 mmol) in an argon atmosphere at 0° C. After stirring at 0° C. for 1 hour, the reaction is quenched by addition of 2N HCl (to pH 2). The methanol is removed in vacuo and the reaction mixture is taken up in ether. The ether solution is washed with saturated $KHCO_3$, saturated NaCl and dried ($MgSO_4$). The ether is evaporated to yield the title C compound.

D.

(1α,2β,3β,4α)-5-[[[3-[2-(Hexyloxy)ethyl]-7-oxabicyclo[2.2.1]hept-2-yl]methyl]thio]pentanoic acid Following the procedure of Example 3, Part D and Example 4 except substituting the above part C alcohol for the Example 1 Part G alcohol used in Example 3 Part D, the title compound is obtained.

EXAMPLE 19

(1α,2β,3β,4α)-4-[2-[3-[2-(Hexyloxy)ethyl]-7-oxabicyclo[2.2.1]hept-2-yl]ethoxy]butanoic acid

A.

(1α,2β,3β,4α)-4-[2-[3-Formyl-7-oxabicyclo[2.2.1]hept-2-yl]ethoxy]butanoic acid, methyl ester Following the procedure of Example 15A except substituting (1α,2β,3β,4α)-4-[2-[3-hydroxymethyl-7-oxabicyclo[2.2.1]hept-2-yl]ethoxy]butanoic acid, methyl ester (prepared as described in Example 11 Part N) for the Example 1 Part G alcohol, the title alcohol is obtained.

B.

(1α,2β,3β,4α)-4-[[2-[3-(2-Oxo)ethyl]-7-oxabicyclo[2.2.1]hept-2-yl]ethoxy]butanoic acid, methyl ester Following the procedure of Example 15 Part B except substituting the above Part A aldehyde for the Example 15 Part A aldehyde, the title compound is obtained.

C.

(1α,2β,3β,4α)-4-[2-[3-(2-Hydroxyethyl)-7-oxabicyclo[2.2.1]hept-2-yl]ethoxy]butanoic acid, methyl ester Following the procedure of Example 15 Part C except substituting the above Part B aldehyde for the Example 15 Part B aldehyde, the title compound is obtained.

D.

(1α,2β,3β,4α)-4-[2-[3-[2-(Hexyloxy)ethyl]-7-oxabicyclo[2.2.1]hept-2-yl]ethoxy]butanoic acid Following the procedure of Examples 1 Part H and Example 2 except substituting the above Part C alcohol for the Example 1 part G alcohol used in Example 1 Part H, the title compound is obtained.

EXAMPLE 20

(1α,2β,3β,4α)-5-[[2-[3-[2-(Hexyloxy)ethyl]-7-oxabicyclo[2.2.1]hept-2-yl]ethyl]thio]pentanoic acid

A.

(1α,2β,3β,4α)-5-[[2-[3-Formyl-7-oxabicyclo[2.2.1]hept-2-yl]ethyl]thio]pentanoic acid, methyl ester Following the procedure of Example 15A except substituting (1α,2β,3β,4α)-4-[2-[3-hydroxymethyl-7-oxabicyclo[2.2.1]hept-2-yl]ethyl]thio]pentanoic acid, methy and ethyl esters (prepared as described in Example 9 Part K) for the Example 1 Part G alcohol, the title compound is obtained.

B.

(1α,2β,3β,4α)-5-[[2-[3-(2-Oxo)ethyl]-7-oxabicyclo[2.2.1]hept-2-yl]ethyl]thio]pentanoic acid, methyl and ethyl esters Following the procedure of Example 15 Part B except substituting the above Part A aldehyde for the Example 15 Part A aldehyde, the title compound is obtained.

C.

(1α,2β,3β,4α)-5-[[2-[3-(2-Hydroxyethyl)-7-oxabicyclo[2.2.1]hept-2-yl]ethyl]thio]pentanoic acid, methyl and ethyl esters Following the procedure of Example 15 Part C except substituting the above Part B aldehyde for the Example 15 Part B aldehyde, the title compound is obtained.

D.

(1α,2β,3β,4α)-5-[[2-[3-[2-(Hexyloxy)ethyl]-7-oxabicyclo[2.2.1]hept-2-yl]ethyl]thio]pentanoic acid Following the procedure of Example 3 Part D and Example 4 except substituting the above Part C alcohol for the Example 3 Part C alcohol, the title compound is obtained.

EXAMPLE 21

(1α,2β,3β,4α)-4-[2-[3-[2-(Hexylthio)ethyl]-7-oxabicyclo[2.2.1]hept-2-yl]ethoxy]butanoic acid

A.

(1α,2β,3β,4α)-4-[2-[3-(2-Hydroxyethyl)-7-oxabicyclo[2.2.1]hept-2-yl]ethoxy]butanoic acid, methyl ester Following the procedure of Example 15 Parts A, B and C except substituting (1α,2β,3β,4α)-4-[2-[3-hydroxymethyl)-7-oxabicyclo[2.2.1]hept-2-yl]ethoxy]butanoic acid, methyl ester (prepared as described in Example 11 Part N) for the Example 1 Part G alcohol, the title compound is obtained.

B.

(1α,2β,3β,4α)-4-[2-[3-[2-(Hexylthio)ethyl]-7-oxabicyclo[2.2.1]hept-2-yl]ethoxy]butanoic acid Following the procedure of Example 17 except substituting (1α,2β,3β,4α)-4-[2-[3-(2-hydroxyethyl)-7-oxabicyclo[2.2.1]hept-2-yl]ethoxy]butanoic acid, methyl ester for the Example 15 Part C alcohol, the title compound is obtained.

EXAMPLE 22

(1α,2β,3β,4α)-5-[[2-[3-[2-(Hexylthio)ethyl]-7-oxabicyclo[2.2.1]hept-2-yl]ethyl]thio]pentanoic acid

A.

(1α,2β,3β,4α)-5-[[2-[3-(2-Hydroxyethyl)-7-oxabicyclo[2.2.1]hept-2-yl]ethyl]thio]pentanoic acid, methyl ester Following the procedure of Example 16A except substituting (1α,2β,3β,4α)-5-[2-[3-(hydroxymethyl)-7-oxabicyclo[2.2.1]hept-2-yl]ethyl]thio]pentanoic acid, methyl and ethyl esters (prepared as described in Example 9 Part K) for the Example 3 Part C alcohol, the title compound is obtained.

B.

(1α,2β,3β,4α)-5-[[2-[3-[2-(Hexylthio)ethyl]-7-oxabicyclo[2.2.1]hept-2-yl]ethyl]thio]pentanoic acid Following the procedure of Example 18 except substituting the above title A alcohol for the Example 16 Part A alcohol, the title compound is obtained.

EXAMPLE 23

[1α,2β(2E),3β,4α]-5-[[3-[(Hexyloxy)methyl]-7-oxabicyclo[2.2.1]hept-2-yl]methoxy]-2-pentenoic acid

A.
(1α,2β,3β,4α)-5-[[3-[(Hexyloxy)methyl]7-oxabicyclo[2.2.1]hept-2-yl]methoxy]2-selenophenyl pentanoic acid, methyl ester To a solution of 308 μl of diisopropylamine (2.2 mmole) in 5 ml of dry THF, cooled at −78° C. is added dropwise 1.25 ml of a 1.6M solution of n-butyllithium in hexane. After 30 minutes at −78° C., a solution of 356 mg of (1α,2β,3β,4α)-5-[[3-[(hexyloxy)methyl]-7-oxabicyclo[2.2.1]hept-2-yl]methoxy]pentanoic acid, hexyl ester, prepared as described in Example 1, (1 mmole) in 2 ml of dry THF is added dropwise. The reaction mixture is stirred for 30 minutes, whereupon a solution of 625 mg of diphenyldiselenide (2 mmole) in 2 ml of dry THF is added. The yellow color of diselenide disappears immediately upon its addition. The yellow solution is stirred at −78° C. for 30 minutes, whereupon the cooling bath was removed. The reaction mixture is then quenched by addition of aqueous ammonium chloride solution. It is then diluted with water and the organic layer is separated. The aqueous layer is extracted with ether. The combined organic extract is dried over anhydrous magnesium sulfate and concentrated in vacuo. Purification by chromatography on a silica gel column and eluting with 5–25% ethyl acetate in hexane gives 600 mg of title α-selenophenyl ester (90% yield).

B.
(1α,2β,3β,4α)-5-[[3-[(Hexyloxy)methyl]-7-oxabicyclo[2.2.1]hept-2-yl]methoxy]2-selenophenyl pentanoic acid A solution of 600 mg of title A α-selenophenyl esters in 10 ml of distilled THF is treated with 5 ml of a 1N aqueous lithium hydroxide solution. After stirring at room temperature for 2 days, the reaction mixture is acidified with 1N aqueous hydrochloric acid solution and extracted with methylene chloride. The methylene chloride extract is dried over anhydrous magnesium sulfate and concentrated in vacuo to yield 560 mg of title acid.

C.
[1α,2β(2E),3β,4α]-5-[[3-[(Hexyloxy)methyl]-7-oxabicyclo[2.2.1]hept-2-yl]methoxy]-2-pentenoic acid A solution of 560 mg of title B acid (0.86 mmole) in 10 ml of distilled THF is treated with 500 ml of a 30% aqueous hydrogen peroxide solution at 0°–5° C. After a few minutes, the cooling bath is removed and the reaction mixture is stirred at room temperature for 1 hour. It is then diluted with methylene chloride and washed thoroughly with water. The organic layer is dried over anhydrous MgSO$_4$ and concentrated under reduced pressure. The crude residue is chromatographed on a CC-7 silica gel column and eluted with 20–60% ethyl acetate in hexane to obtain the title α,β-unsaturated acid.

EXAMPLE 24

[1α,2β(2E),3β,4α]-5-[[[3-[(Hexyloxy)methyl]-7-oxabicyclo[2.2.1]hept-2-yl]methyl]thio]-2-pentenoic acid Following the procedure of Example 3 and 4 except substituting ethyl-5-bromo-2-pentenoate for ethyl-5-bromo valerate in Example 3 Part C, the title compound is obtained.

EXAMPLE 25

[1α,2β(2E),3β,4α]-5-[[3-[(Hexylthio)methyl]-7-oxabicyclo[2.2.1]hept-2-yl]methoxy]-2-pentenoic acid Following the procedure of Examples 1 Parts A–G and 5 except substituting 5-t-butyldimethylsilyloxy 3-pentenyl mesylate for 5-t-butyldimethylsilyloxy pentyl mesylate in Example 1 Part C, the title compound is obtained.

EXAMPLE 26

[1α,2β(2E),3β,4α]-5-[[[3-[(Hexylthio)methyl]-7-oxabicyclo[2.2.1]hept-2-yl]methyl]thio]-2pentenoic acid Followiing the procedure of Examples 3 Parts A–C and 7 except substituting ethyl-5-bromo-2-pentenoate for ethyl-5-bromovalerate in Example 3 Part C, the title compound is obtained.

EXAMPLE 27

(1α,2β,3β,4α)-5-[2-[3-[(Hexyloxy)methyl]-7-oxabicyclo[2.2.1]hept-2-yl]ethyl]thio]-2-pentenoic acid Following the procedure of Examples 3 and 4 except substituting ethyl-5-bromo-2-pentenoate for ethyl-5-bromovalerate in Example 3 Part C, the title compound is obtained.

EXAMPLE 28

[1α,2β(2E),3β,4α]-4-[[3-[(Hexyloxy)methyl]-7-oxabicyclo[2.2.1]hept-2-yl]methoxy]-2-butenoic acid Following the procedure of Example 23 except substituting the Example 11 ester compound for the Example 1 compound in Example 23 Part A, the title compound is obtained.

EXAMPLE 29

[1α,2β(2E),3β,4α]-5-[[2-[3-[(Hexyloxy)methyl]-7-oxabicyclo[2.2.1]hept-2-yl]ethyl]thio]-2-pentenoic acid Following the procedure of Examples 9 and 10 except substituting ethyl-5-bromo 2-pentenoate for ethyl 5-bromovalerate in Example 9 Part K, the title compound is obtained.

EXAMPLE 30

[1α,2β(2E),3β,4α]-4-[2-[3-[(Hexylthio)methyl]-7-oxabicyclo[2.2.1]hept-2-yl]ethoxy]-2-butenoic acid

A.
[1α,2β(2E),3β,4α]-4-[2-[3-Hydroxymethyl-7-oxabicyclo[2.2.1]hept-2-yl]ethoxy]2-butenoic acid, methyl ester Following the procedure of Example 11 Parts A to J except substituting 4-t-butylsilyloxy 2-butenyl mesylate for 4-t-butylsilyloxybutyl mesylate in Example 11 Part D, the title compound is obtained.

B.
[1α,2β(2E),3β,4α]-4-[2-[3-[(Hexylthio)methyl]-7-oxabicyclo[2.2.1]hept-2-yl]ethoxy]-2-butenoic acid Following the procedure of Examples 5 and 6 except substituting Example 30 title A ester for Example 1 Part G ester, the title compound is obtained.

EXAMPLE 31

[1α,2β(2E),3β,4α]-5-[[3-[2-(Hexyloxy)ethyl]-7-oxabicyclo[2.2.1]hept-2-yl]methoxy]-2-pentenoic acid Following the procedure of Example 23 except substituting the Example 15 ester compound for the Example 1 compound in Example 23 Part A, the title compound is obtained.

EXAMPLE 32

[1α,2β(2E),3β,4α]-5-[[[3-[2-(Hexyloxy)ethyl]-7-oxabicyclo[2.2.1]hept-2-yl]methyl]thio]-2-pentenoic acid

A.

[1α,2β(2E),3β,4α]-5-[[[3-Hydroxymethyl-7-oxabicyclo[2.2.1]hept-2-yl]methyl]thio]-2-pentenoic acid, methyl ester and ethyl ester Following the procedure of Example 3 Parts A to C except substituting ethyl-5-bromo-2-pentenoate for ethyl-5-bromovalerate in Example 3 Part C, the title alcohol is obtained.

B.

[1α,2β(2E),3β,4α]-5-[[[3-[2-Hydroxyethyl]-7-oxabicyclo[2.2.1]hept-2-yl]methyl]thio]-2-pentenoic acid, methyl and ethyl esters Following the procedure of Example 18 Parts A to C except substituting Example 32 Part A alcohol for Example 3 Part C alcohol in Example 18 Part A, the title alcohol is obtained.

C.

[1α,2β(2E),3β,4α]-5-[[[3-[2-(Hexyloxy)ethyl]-7-oxabicyclo[2.2.1]hept-2-yl]methyl]thio]-2-pentenoic acid Following the procedure of Examples 15 Part D and 16 except substituting Example 32 Part B alcohol for Example 15 Part C alcohol, the title acid is obtained.

EXAMPLE 33

[1α,2β(2E),3β,4α]-5-[[3-[2-(Hexyloxy)ethyl]-7-oxabicyclo[2.2.1]hept-2-yl]methoxy]-2-pentenoic acid

A.

[1α,2β(2E),3β,4α]-5-[[3-Hydroxymethyl-7-oxabicyclo[2.2.1]hept-2-yl]methoxy]2-pentenoic acid, methyl ester Following the procedure of Example 1 Parts A to G except substituting 5-t-butyldimethylsilyloxy 3-pentenyl mesylate for 5-t-butyldimethylsilyloxypentyl mesylate in Example 1 Part C, the title alcohol is obtained.

B.

[1α,2β(2E),3β,4α]-5-[[3-(2-Hydroxyethyl)-7-oxabicyclo[2.2.1]hept-2-yl]methoxy]-2-pentenoic acid, methyl ester Following the procedure of Example 15 Parts A to C except substituting Example 33 Part A alcohol for the Example 1 Part G alcohol in Example 15 Part A, the title alcohol is obtained.

C.

[1α,2β(2E),3β,4α]-5-[[3-[2-(Hexylthio)ethyl]-7-oxabicyclo[2.2.1]hept-2-yl]methoxy]-2-pentenoic acid Following the procedure of Examples 5 and 6 except substituting the Example 33 Part B alcohol for the Example 1 Part G alcohol in Example 5 Part A, the title acid is obtained.

EXAMPLE 34

[1α,2β(2E),3β,4α]-5-[[[3-[2-(Hexylthio)ethyl]-7-oxabicyclo[2.2.1]hept-2-yl]methyl]thio]-2-pentenoic acid Following the procedure of Examples 5 and 6 except substituting Example 32 part B alcohol for Example 1 Part G alcohol, the title acid is obtained.

EXAMPLE 35

[1α,2β(2E),3β,4α]-4-[2-[3-[2-(Hexyloxy)ethyl]-7-oxabicyclo[2.2.1]hept-2-yl]ethoxy]-2-butenoic acid Following the procedure of Example 23 except substituting the Example 19 ester compound for the Example 1 compound in Example 23 Part A, the title compound is obtained.

EXAMPLE 36

[1α,2β(2E),3β,4α]-5-[[2-[3-[2-(Hexyloxy)ethyl]-7-oxabicyclo[2.2.1]hept-2-yl]ethyl]thio]-2-pentenoic acid

A.

[1α,2β(2E),3β,4α]-5-[[2-[3-Hydroxymethyl-7-oxabicyclo[2.2.1]hept-2-yl]ethyl]thio]-2-pentenoic acid, ethyl ester Following the procedure of Example 9 Parts A to K except substituting ethyl-5-bromo 2-pentenoate for ethyl 5-bromovalerate in Example 9 Part K, the title alcohol is obtained.

B.

[1α,2β(2E),3β,4α]-5-[[2-[3-(2-Hydroxyethyl)-7-oxabicyclo[2.2.1]hept-2-yl]ethyl]thio]-2-pentenoic acid, ethyl ester Following the procedure of Example 18 Parts A to C except substituting Example 36 Part A alcohol for Example 3 Part C alcohol in Example 18 Part A, the title alcohol is obtained.

C.

[1α,2β(2E),3β,4α]-5-[[2-[3-[(Hexyloxy)ethyl]-7-oxabicyclo[2.2.1]hept-2-yl]ethyl]thio]-2-pentenoic acid Following the procedure of Examples 1 Part H and 2 except substituting Example 36 Part B alcohol for Example 1 Part G alcohol in Example 1 Part H, the title acid is obtained.

EXAMPLE 37

[1α,2β(2E),3β,4α]-4-[2-(3-[2-(Hexylthio)ethyl]-7-oxabicyclo[2.2.1]hept-2-yl]ethoxy]-2-butenoic acid

A.

[1α,2β(2E),3β,4α]-4-[[3-Hydroxymethyl-7-oxabicyclo[2.2.1]hept-2-yl]ethoxy]-2-pentenoic acid, methyl ester Following the procedure of Example 11 Parts A to N except substituting 4-t-butyldimethylsilyloxy 2-butenyl mesylate for 4-t-butyldimethylsilyloxybutyl mesylate in Example 11 Part J, the title alcohol is obtained.

B.

[1α,2β(2E),3β,4α]-4-[2-[3-[2-(Hexylthio)ethyl]-7-oxabicyclo[2.2.1]hept-2-yl]ethoxy]-2-butenoic acid Following the procedure of Examples 18 and 19 except substituting Example 37 Part A alcohol for Example 3 Part C alcohol in Example 18 Part A, the title acid is obtained.

EXAMPLE 38

[1α,2β(2E),3β,4α]-5-[[2-[3-[2-(Hexylthio)ethyl]-7-oxabicyclo[2.2.1]hept-2-yl]ethyl]thio]-2-pentenoic acid Following the procedure of Examples 5 and 6 except substituting Example 36 Part B alcohol for Example 1 Part G alcohol in Example 5 Part A, the title acid is obtained.

EXAMPLE 39

(1α,2β,3β,4α)-5-[[3-(Methyloxymethyl)-7-oxabicyclo[2.2.1]hept-2-yl]methoxy]pentanoic acid Following the procedure of Examples 1 and 2 except substituting methyl mesylate for hexyl mesylate, the title compound is obtained.

EXAMPLE 40

(1α,2β,3β,4α)-5-[[3-[(2-Propenyloxy)methyl]-7-oxabicyclo[2.2.1]hept-2-yl]methoxy]pentanoic acid Following the procedure of Examples 1 and 2 except substituting 2-propenyl mesylate for hexyl mesylate, the title compound is obtained.

EXAMPLE 41

(1α,2β,3β,4α)-5-[[3-(2-Butenyloxy)methyl]-7-oxabicyclo[2.2.1]hept-2-yl]methoxy]pentanoic acid Following the procedure of Examples 1 and 2 except substituting 2-butenyl mesylate for hexyl mesylate, the title compound is obtained.

EXAMPLE 42

(1α,2β,3β,4α)-5-[[3-[(Benzyloxy)methyl]-7-oxabicyclo[2.2.1]hept-2-yl]methoxy]pentanoic acid Following the procedure of Examples 1 and 2 except substituting benzyl mesylate for hexyl mesylate, the title compound is obtained.

EXAMPLE 43

(1α,2β,3β,4α)-5-[[3-[(Phenyloxy)methyl]-7-oxabicyclo[2.2.1]hept-2-yl]methoxy]pentanoic acid (a) Phenol (1 mmol) is added to a solution of triphenylphosphine (1 mmol), diethylazodicarboxylate (1 mmol) and title G alcohol from Example 1 (1 mmol) in 25 ml THF and is stirred under an argon atmosphere for 48 hours at 23° C. The reaction mixture is concentrated in vacuo. The residue is triturated with ether and the solids are removed. The filtrate is concentrated in vacuo and chromatographed on silica gel to give (1α,2β,3β,4α)-5-[[3-[(phenyloxy)methyl]-7-oxabicyclo[2.2.1]hept-2-yl]methoxy]pentanoic acid, methyl ester.

(b) Following the procedure as set out in Example 2, the ester from part (a) is converted to the title compound.

EXAMPLE 44

(1α,2β,3β,4α)-5-[[3-[(Cyclohexyloxy)methyl]-7-oxabicyclo[2.2.1]hept-2-yl]methoxy]pentanoic acid Following the procedure of Examples 1 and 2 except substituting cyclohexylmesylate for hexyl mesylate, the title compound is obtained.

EXAMPLE 45

(1α,2β,3β,4α)-5-[[3-[(Cyclopentylmethoxy)methyl]-7-oxabicyclo[2.2.1]hept-2-yl]methoxy]pentanoic acid Following the procedure of Examples 1 and 2 except substituting cyclopentylmethyl mesylate for hexyl mesylate, the title compound is obtained.

EXAMPLE 46

(1α,2β,3β,4α)-5-[[3-[(Benzyloxy)methyl]-7-oxabicyclo[2.2.1]hept-2-yl]methyl]thio]pentanoic acid Following the procedure of Examples 3 and 4 except substituting benzyl mesylate for hexyl mesylate, the title compound is obtained.

EXAMPLE 47

(1α,2β,3β,4α)-5-[[[3-[(2-Butenyloxy)methyl]-7-oxabicyclo[2.2.1]hept-2-yl]methyl]thio]pentanoic acid Following the procedure of Examples 3 and 4 except substituting 2-butenyl mesylate for hexyl mesylate, the title compound is obtained.

EXAMPLE 48

(1α,2β,3β,4α)-5-[[[3-[(Cyclohexyloxy)methyl]-7-oxabicyclo[2.2.1]hept-2-yl]methyl]thio]pentanoic acid Following the procedure of Examples 3 and 4 except substituting cyclohexyl mesylate for hexyl mesylate, the title compound is obtained.

EXAMPLE 49

(1α,2β,3β,4α)-5-[[[3-[(Cyclopentylmethyloxy)methyl]-7-oxabicyclo[2.2.1]hept-2-yl]methyl]thio]pentanoic acid Following the procedure of Examples 3 and 4 except substituting cyclopentylmethyl mesylate for hexyl mesylate, the title compound is obtained.

EXAMPLE 50

(1α,2β,3β,4α)-5-[[3-[(Phenyloxy)methyl]-7-oxabicyclo[2.2.1]hept-2-yl]methylthio]pentanoic acid Following the procedure of Examples 43 and 3 except substituting the Example 3 Part C alcohol for the Example 1 Part G alcohol, the title compound is obtained.

EXAMPLE 51

(1α,2β,3β,4α)-5-[[3-[(2-Pentylthio)methyl]-7-oxabicyclo[2.2.1]hept-2-yl]methoxy]pentanoic acid Following the procedure of Examples 5 and 6 except substituting 2-pentylmercaptan for 1-hexanethiol, the title compound is obtained.

EXAMPLE 52

(1α,2β,3β,4α)-5-[[3-[(Benzylthio)methyl]-7-oxabicyclo[2.2.1]hept-2-yl]methoxy]pentanoic acid Following the procedure of Examples 5 and 6 except substituting benzylmercaptan for 1-hexanethiol, the title compound is obtained.

EXAMPLE 53

(1α,2β,3β,4α)-5-[[[3-[(Cyclohexylthio)methyl]-7-oxabicyclo[2.2.1]hept-2-yl]methoxy]pentanoic acid Following the procedure of Examples 5 and 6 except substituting cyclohexylmercaptan for 1-hexanethiol, the title compound is obtained.

EXAMPLE 54

(1α,2β,3β,4α)-5-[[[3-[(Phenylthio)methyl]-7-oxabicyclo[2.2.1]hept-2-yl]methoxy]pentanoic acid Following the procedure of Examples 5 and 6 except substituting phenylmercaptan for 1-hexanethiol, the title compound is obtained.

EXAMPLE 55

(1α,2β,3β,4α)-5-[[[3-[(Cyclopentylthio)methyl]-7-oxabicyclo[2.2.1]hept-2-yl]methyl]thio]pentanoic acid Following the procedure of Examples 7 and 8 except substituting cyclopentylmercaptan for 1-hexanethiol, the title compound is obtained.

EXAMPLE 56

(1α,2β,3β,4α)-5-[[[3-[(Cyclohexylmethylthio)methyl]-7-oxabicyclo[2.2.1]hept-2-yl]methyl]thio]pentanoic acid Following the procedure of Examples 7 and 8 except substituting cyclohexylmethylmercaptan for 1-hexanethiol, the title compound is obtained.

EXAMPLE 57

(1α,2β,3β,4α)-5-[[[3-[(Phenylthio)methyl]-7-oxabicyclo[2.2.1]hept-2-yl]methyl]thio]pentanoic acid Following the procedure of Examples 7 and 8 except substituting phenylmercaptan for 1-hexanethiol, the title compound is obtained.

EXAMPLE 58

(1α,2β,3β,4α)-5-[[[3-[(Benzylthio)methyl]-7-oxabicyclo[2.2.1]hept-2-yl]methyl]thio]pentanoic acid Following the procedure of Examples 7 and 8 except substituting benzylmercaptan for 1-hexanethiol, the title compound is obtained.

EXAMPLE 59

(1α,2β,3β,4α)-5-[[[3-[(3-Pentenylthio)methyl]-7-oxabicyclo[2.2.1]hept-2-yl]methyl]thio]pentanoic acid Following the procedure of Examples 7 and 8 except substituting 1-(3-pentenyl)mercaptan for 1-hexanethiol, the title compound is obtained.

EXAMPLE 60

(1α,2β,3β,4α)-5-[[2-[3-[(Cyclohexyloxy)methyl]-7-oxabicyclo[2.2.1]hept-2-yl]ethyl]thio]pentanoic acid Following the procedure of Examples 9 and 10 except substituting cyclohexyl mesylate for hexyl mesylate, the title compound is obtained.

EXAMPLE 61

(1α,2β,3β,4α)-5-[[2-[3-[(Cyclopentylmethyloxy)methyl]-7-oxabicyclo[2.2.1]hept-2-yl]ethyl]thio]pentanoic acid Following the procedure of Examples 9 and 10 except substituting cyclopentylmethyl mesylate for hexyl mesylate, the title compound is obtained.

EXAMPLE 62

(1α,2β,3β,4α)-5-[[2-[3-[(2-Butenyloxy)methyl]-7-oxabicyclo[2.2.1]hept-2-yl]ethyl]thio]pentanoic acid Following the procedure of Examples 9 and 10 except substituting 2-butenyl mesylate for hexyl mesylate, the title compound is obtained.

EXAMPLE 63

(1α,2β,3β,4α)-5-[[2-[3-[(Phenyloxy)methyl]-7-oxabicyclo[2.2.1]hept-2-yl]ethyl]thio]pentanoic acid Following the procedure of Examples 43 and 3 except substituting the Example 9 Part K alcohol for the Example 1 Part G alcohol, the title compound is obtained.

EXAMPLE 64

(1α,2β,3β,4α)-4-[2-[3-[(Cyclohexyloxy)methyl]-7-oxabicyclo[2.2.1]hept-2-yl]ethoxy]butanoic acid Following the procedure of Examples 11 and 12 except substituting cyclohexyl mesylate for hexyl mesylate, the title compound is obtained.

EXAMPLE 65

(1α,2β,3β,4α)-4-[2-[3-[(2-Pentenyloxy)methyl]-7-oxabicyclo[2.2.1]hept-2-yl]ethoxy]butanoic acid Following the procedure of Examples 11 and 12 except substituting 2-pentenyl mesylate for hexyl mesylate, the title compound is obtained.

EXAMPLE 66

(1α,2β,3β,4α)-4-[2-[3-[(Benzyloxy)methyl]-7-oxabicyclo[2.2.1]hept-2-yl]ethoxy]butanoic acid Following the procedure of Examples 11 and 12 except substituting benzyl mesylate for hexyl mesylate, the title compound is obtained.

EXAMPLE 67

(1α,2β,3β,4α)-4-[2-[3-[(Phenyloxy)methyl]-7-oxabicyclo[2.2.1]hept-2-yl]ethoxy]butanoic acid Following the procedure of Examples 43 and 3 except substituting the Example 11 Part H alcohol for the Example 1 Part C alcohol, the title compound is obtained.

EXAMPLE 68

(1α,2β,3β,4α)-4-[2-[3-[(Cyclopentylmethyloxy)methyl]-7-oxabicyclo[2.2.1]hept-2-yl]ethoxy]butanoic acid Following the procedure of Examples 11 and 12 except substituting cyclopentylmethyl mesylate for hexyl mesylate, the title compound is obtained.

EXAMPLE 69

(1α,2β,3β,4α)-5-[[2-[3-[(Benzylthio)methyl]-7-oxabicyclo[2.2.1]hept-2-yl]ethyl]thio]pentanoic acid Following the procedure of Example 13 except substituting benzylmercaptan for 1-hexanethiol, the title compound is obtained.

EXAMPLE 70

(1α,2β,3β,4α)-5-[[2-[3-[(Phenylthio)methyl]-7-oxabicyclo[2.2.1]hept-2-yl]ethyl]thio]pentanoic acid Following the procedure of Example 13 except substituting phenylmercaptan for 1-hexanethiol, the title compound is obtained.

EXAMPLE 71

(1α,2β,3β,4α)-5-[[2-[3-[(Cycloheptylthio)methyl]-7-oxabicyclo[2.2.1]hept-2-yl]ethyl]thio]pentanoic acid Following the procedure of Example 13 except substituting cycloheptylmercaptan for 1-hexanethiol, the title compound is obtained.

EXAMPLE 72

(1α,2β,3β,4α)-5-[[2-[3-[(Cyclohexylmethylthio)methyl]-7-oxabicyclo[2.2.1]hept-2-yl]ethyl]thio]pentanoic acid Following the procedure of Example 13 except substituting cyclohexylmethylmercaptan for 1-hexanethiol, the title compound is obtained.

EXAMPLE 73

(1α,2β,3β,4α)-5-[[2-[3-[(2-Propenylthio)methyl]-7-oxabicyclo[2.2.1]hept-2-yl]ethyl]thio]pentanoic acid Following the procedure of Example 13 except substituting 2-propenylthiol for 1-hexanethiol, the title compound is obtained.

EXAMPLE 74

(1α,2β,3β,4α)-5-[2-[3-[(Benzylthio)methyl]-7-oxabicyclo[2.2.1]hept-2-yl]ethoxy]butanoic acid Following the procedure of Example 14 except substituting benzylmercaptan for 1-hexanethiol, the title compound is obtained.

EXAMPLE 75

(1α,2β,3β,4α)-5-[2-[3-[(Phenylthio)methyl]-7-oxabicyclo[2.2.1]hept-2-yl]ethoxy]butanoic acid Following the procedure of Example 14 except substituting phenylmercaptan for 1-hexanethiol, the title compound is obtained.

EXAMPLE 76

(1α,2β,3β,4α)-5-[2-[3-[(3-Pentenylthio)methyl]-7-oxabicyclo[2.2.1]hept-2-yl]ethoxy]butanoic acid Following the procedure of Example 14 except substituting 3-pentenylthiol for 1-hexanethiol, the title compound is obtained.

EXAMPLE 77

(1α,2β,3β,4α)-5-[2-[3-[(Cyclohexylthio)methyl]-7-oxabicyclo[2.2.1]hept-2-yl]ethoxy]butanoic acid Following the procedure of Example 14 except substituting cyclohexylmercaptan for 1-hexanethiol, the title compound is obtained.

EXAMPLE 78

(1α,2β,3β,4α)-5-[[3-[2-(Benzyloxy)ethyl]-7-oxabicyclo[2.2.1]hept-2-yl]methoxy]pentanoic acid Following the procedure of Example 15 except substituting benzyl mesylate for hexyl mesylate, the title compound is obtained.

EXAMPLE 79

(1α,2β,3β,4α)-5-[[3-[2-(Phenyloxy)ethyl]-7-oxabicyclo[2.2.1]hept-2-yl]methoxy]pentanoic acid Following the procedure of Example 15 except substituting phenyl mesylate for hexyl mesylate, the title compound is obtained.

EXAMPLE 80

(1α,2β,3β,4α)-5-[[3-[2-(3-Butenyloxy)ethyl]-7-oxabicyclo[2.2.1]hept-2-yl]methoxy]pentanoic acid Following the procedure of Example 15 except substituting 1-butenyl mesylate for hexyl mesylate, the title compound is obtained.

EXAMPLE 81

(1α,2β,3β,4α)-5-[[3-[2-(Cyclohexyloxy)ethyl]-7-oxabicyclo[2.2.1]hept-2-yl]methoxy]pentanoic acid Following the procedure of Example 15 except substituting cyclohexyl mesylate for hexyl mesylate, the title compound is obtained.

EXAMPLE 82

(1α,2β,3β,4α)-5-[[3-[2-(Propyloxy)ethyl]-7-oxabicyclo[2.2.1]hept-2-yl]methoxy]pentanoic acid Following the procedure of Example 15 except substituting n-propyl mesylate for hexyl mesylate, the title compound is obtained.

EXAMPLE 83

(1α,2β,3β,4α)-5-[[[3-[2-(Benzyloxy)ethyl]-7-oxabicyclo[2.2.1]hept-2-yl]methyl]thio]pentanoic acid Following the procedure of Example 16 except substituting benzyl mesylate for hexyl mesylate, the title compound is obtained.

EXAMPLE 84

(1α,2β,3β,4α)-5-[[[3-[2-(Phenyloxy)ethyl]-7-oxabicyclo[2.2.1]hept-2-yl]methyl]thio]pentanoic acid Following the procedure of Example 43 except substituting the Example 16 Part A alcohol for the Example 1 Part G alcohol, the title compound is obtained.

EXAMPLE 85

(1α,2β,3β,4α)-5-[[[3-[2-(Cyclohexyloxy)ethyl]-7-oxabicyclo[2.2.1]hept-2-yl]methyl]thio]pentanoic acid Following the procedure of Example 16 except substituting cyclohexyl mesylate for hexyl mesylate, the title compound is obtained.

EXAMPLE 86

(1α,2β,3β,4α)-5-[[[3-[2-(Cyclopentylmethyloxy)ethyl]-7-oxabicyclo[2.2.1]hept-2-yl]methyl]thio]pentanoic acid Following the procedure of Example 16 except substituting cyclopentylmethyl mesylate for hexyl mesylate, the title compound is obtained.

EXAMPLE 87

(1α,2β,3β,4α)-5-[[[3-[2-(2-Pentenyloxy)ethyl]-7-oxabicyclo[2.2.1]hept-2-yl]methyl]thio]pentanoic acid Following the procedure of Example 16 except substituting 2-pentenyl mesylate for hexyl mesylate, the title compound is obtained.

EXAMPLE 88

(1α,2β,3β,4α)-5-[[[3-[2-(Pentylthio)ethyl]-7-oxabicyclo[2.2.1]hept-2-yl]methyl]thio]pentanoic acid Following the procedure of Example 17 except substituting 1-pentanethiol for 1-hexanethiol, the title compound is obtained.

EXAMPLE 89

(1α,2β,3β,4α)-5-[[[3-[2-(Benzylthio)ethyl]-7-oxabicyclo[2.2.1]hept-2-yl]methyl]thio]pentanoic acid Following the procedure of Example 17 except substituting benzylthiol for 1-hexanethiol, the title compound is obtained.

EXAMPLE 90

(1α,2β,3β,4α)-5-[[[3-[2-(Phenylthio)ethyl]-7-oxabicyclo[2.2.1]hept-2-yl]methyl]thio]pentanoic acid Following the procedure of Example 17 except substituting phenylmercaptan for 1-hexanethiol, the title compound is obtained.

EXAMPLE 91

(1α,2β,3β,4α)-5-[[[3-[2-(Cyclohexylthio)ethyl]-7-oxabicyclo[2.2.1]hept-2-yl]methyl]thio]pentanoic acid Following the procedure of Example 17 except substituting cyclohexylmercaptan for 1-hexanethiol, the title compound is obtained.

EXAMPLE 92

(1α,2β,3β,4α)-5-[[[3-[2-(Benzylthio)ethyl]-7-oxabicyclo[2.2.1]hept-2-yl]methyl]thio]pentanoic acid Following the procedure of Example 18 except substituting benzylmercaptan for 1-hexanethiol, the title compound is obtained.

EXAMPLE 93

(1α,2β,3β,4α)-5-[[[3-[2-(Cycloheptylthio)ethyl]-7-oxabicyclo[2.2.1]hept-2-yl]methyl]thio]pentanoic acid Following the procedure of Example 18 except substituting cycloheptylmercaptan for 1-hexanethiol, the title compound is obtained.

EXAMPLE 94

(1α,2β,3β,4α)-5-[[[3-[2-(Phenylthio)ethyl]-7-oxabicyclo[2.2.1]hept-2-yl]methyl]thio]pentanoic acid Following the procedure of Example 18 except substituting phenylmercaptan for 1-hexanethiol, the title compound is obtained.

EXAMPLE 95

(1α,2β,3β,4α)-5-[[[3-[2-(Cyclohexylmethylthio)ethyl]-7-oxabicyclo[2.2.1]hept-2-yl]methyl]thio]pentanoic acid Following the procedure of Example 18 except substituting cyclohexylmethylmercaptan for 1-hexanethiol, the title compound is obtained.

EXAMPLE 96

(1α,2β,3β,4α)-5-[[[3-[2-(2-Propenylthio)ethyl]-7-oxabicyclo[2.2.1]hept-2-yl]methyl]thio]pentanoic acid Following the procedure of Example 18 except substituting 1-(2-propenyl)thiol for 1-hexanethiol, the title compound is obtained.

EXAMPLE 97

(1α,2β,3β,4α)-4-[2-[3-[2-(Heptyloxy)ethyl]-7-oxabicyclo[2.2.1]hept-2-yl]ethoxy]butanoic acid Following the procedure of Example 19 except substituting heptyl mesylate for hexyl mesylate, the title compound is obtained.

EXAMPLE 98

(1α,2β,3β,4α)-4-[2-[3-[2-(Benzyloxy)ethyl]-7-oxabicyclo[2.2.1]hept-2-yl]ethoxy]butanoic acid Following the procedure of Example 19 except substituting benzyl mesylate for hexyl mesylate, the title compound is obtained.

EXAMPLE 99

(1α,2β,3β,4α)-4-[[2-[3-[2-(Phenylthio)ethyl]-7-oxabicyclo[2.2.1]hept-2-yl]ethoxy]butanoic acid Following the procedure of Example 19 except substituting phenyl mesylate for hexyl mesylate, the title compound is obtained.

EXAMPLE 100

(1α,2β,3β,4α)-4-[2-[3-[2-(Cyclohexyloxy)ethyl]-7-oxabicyclo[2.2.1]hept-2-yl]ethoxy]butanoic acid Following the procedure of Example 19 except substituting cyclohexyl mesylate for hexyl mesylate, the title compound is obtained.

EXAMPLE 101

(1α,2β,3β,4α)-4-[2-[3-[2-(2-Cyclopentylethyloxy)ethyl]-7-oxabicyclo[2.2.1]hept-2-yl]ethoxy]butanoic acid Following the procedure of Example 19 except substituting cyclopentylethyl mesylate for hexyl mesylate, the title compound is obtained.

EXAMPLE 102

(1α,2β,3β,4α)-5-[[2-[3-[2-(Benzyloxy)ethyl]-7-oxabicyclo[2.2.1]hept-2-yl]ethyl]thio]pentanoic acid Following the procedure of Example 20 except substituting benzyl mesylate for hexyl mesylate, the title compound is obtained.

EXAMPLE 103

(1α,2β,3β,4α)-5-[[2-[3-[2-(Phenyloxy)ethyl]-7-oxabicyclo[2.2.1]hept-2-yl]ethyl]thio]pentanoic acid Following the procedure of Example 43 except substituting the Example 20 Part C alcohol for the Example 1 Part G alcohol, the title compound is obtained.

EXAMPLE 104

(1α,2β,3β,4α)-5-[[2-[3-[2-(Cyclopentyloxy)ethyl]-7-oxabicyclo[2.2.1]hept-2-yl]ethyl]thio]pentanoic acid Following the procedure of Example 20 except substituting cyclopentyl mesylate for hexyl mesylate, the title compound is obtained.

EXAMPLE 105

(1α,2β,3β,4α)-4-[[2-[3-[2-(3-Hexenyloxy)ethyl]-7-oxabicyclo[2.2.1]hept-2-yl]ethyl]thio]pentanoic acid Following the procedure of Example 20 except substituting 3-hexenyl mesylate for hexyl mesylate, the title compound is obtained.

EXAMPLE 106

(1α,2β,3β,4α)-4-[[2-[3-[2-(Cyclopropylmethyloxy)ethyl]-7-oxabicyclo[2.2.1]hept-2-yl]ethyl]thio]pentanoic acid Following the procedure of Example 20 except substituting cyclopropylmethyl mesylate for hexyl mesylate, the title compound is obtained.

EXAMPLE 107

(1α,2β,3β,4α)-4-[2-[3-[2-(Benzylthio)ethyl]-7-oxabicyclo[2.2.1]hept-2-yl]ethoxy]butanoic acid Following the procedure of Example 21 except substituting benzylmercaptan for 1-hexanethiol, the title compound is obtained.

EXAMPLE 108

(1α,2β,3β,4α)-4-[2-[3-[2-(Phenylthio)ethyl]-7-oxabicyclo[2.2.1]hept-2-yl]ethoxy]butanoic acid Following the procedure of Example 21 except substituting phenylmercaptan for 1-hexanethiol, the title compound is obtained.

EXAMPLE 109

(1α,2β,3β,4α)-4-[2-[3-[2-(Cyclohexylthio)ethyl]-7-oxabicyclo[2.2.1]hept-2-yl]ethoxy]butanoic acid Following the procedure of Example 21 except substituting cyclohexylmercaptan for 1-hexanethiol, the title compound is obtained.

EXAMPLE 110

(1α,2β,3β,4α)-4-[2-[3-[2-(2-Heptenylthio)ethyl]-7-oxabicyclo[2.2.1]hept-2-yl]ethoxy]butanoic acid Following the procedure of Example 21 except substituting 1-(2-heptenyl)thiol for 1-hexanethiol, the title compound is obtained.

EXAMPLE 111

(1α,2β,3β,4α)-4-[2-[3-[2-(Cyclopentylmethylthio)ethyl]-7-oxabicyclo[2.2.1]hept-2-yl]ethoxy]butanoic acid Following the procedure of Example 21 except substituting cyclopentylmethylmercaptan for 1-hexanethiol, the title compound is obtained.

EXAMPLE 112

(1α,2β,3β,4α)-5-[[2-[3-[2-(Benzylthio)ethyl]-7-oxabicyclo[2.2.1]hept-2-yl]ethyl]thio]pentanoic acid Following the procedure of Example 22 except substituting benzylmercaptan for 1-hexanethiol, the title compound is obtained.

EXAMPLE 113

(1α,2β,3β,4α)-5-[[2-[3-[2-(Phenylthio)ethyl]-7-oxabicyclo[2.2.1]hept-2-yl]ethyl]thio]pentanoic acid Following the procedure of Example 22 except substituting phenylmercaptan for 1-hexanethiol, the title compound is obtained.

EXAMPLE 114

(1α,2β,3β,4α)-5-[[2-[3-[2-(Cyclohexylthio)ethyl]-7-oxabicyclo[2.2.1]hept-2-yl]ethyl]thio]pentanoic acid Following the procedure of Example 22 except substituting cyclohexylmercaptan for 1-hexanethiol, the title compound is obtained.

EXAMPLE 115

(1α,2β,3β,4α)-5-[[2-[3-[2-(2-Hexenylthio)ethyl]-7-oxabicyclo[2.2.1]hept-2-yl]ethyl]thio]pentanoic acid Following the procedure of Example 22 except substituting 1-(2-hexenyl)thiol for 1-hexanethiol, the title compound is obtained.

EXAMPLE 116

(1α,2β,3β,4α)-5-[[2-[3-[2-(Butylthio)ethyl]-7-oxabicyclo[2.2.1]hept-2-yl]ethyl]thio]pentanoic acid Following the procedure of Example 22 except substituting 1-butylthiol for 1-hexanethiol, the title compound is obtained.

EXAMPLE 117

(1α,2β,3β,4α)-5-[[3-[4-(Hexyloxy)butyl-7-oxabicyclo[2.2.1]hept-2-yl]methoxy]pentanoic acid

A.

(1α,2β,3β,4α)-5-[3-(3-Oxo)propyl]-7-oxabicyclo[2.2.1]hept-2-yl]methoxy]pentanoic acid, methyl ester Following the procedure of Example 15 Part B except substituting (1α,2β,3β,4α)-5-[3-(2-oxo)ethyl-7-oxabicyclo[2.2.1]hept-2-yl]methoxy]pentanoic acid, methyl ester for (1α,2β,3β,4α)-7-[3-formyl-7-oxabicyclo[2.2.1]hept-2-yl]methoxy]pentanoic acid, methyl ester, the title A compound is obtained.

B.

(1α,2β,3β,4α)-5-[[3-(4-Oxo)butyl-7-oxabicyclo[2.2.1]hept-2-yl]methoxy]pentanoic acid, methyl ester Following the procedure of Example 20 Part B except substituting the aldehyde from Part A above for (1α,2β,3β,4α)-5-[3-formyl-7-oxabicyclo[2.2.1]hept-2-yl]methoxy]pentanoic acid, methyl ester, the title B aldehyde is obtained.

C.

(1α,2β,3β,4α)-5-[[3-(4-Hydroxybutyl)-7-oxabicyclo[2.2.1]hept-2-yl]methoxy]pentanoic acid, methyl ester Following the procedure of Example 15 Part C except substituting the title B aldehyde for (1α,2β,3β,4α)-5-[3-(2-oxo)ethyl-7-oxabicyclo[2.2.1]hept-2-yl]methoxy]pentanoic acid, methyl ester, the title C alcohol is obtained.

D.

(1α,2β,3β,4α)-5-[[3-[4-(Hexyloxy)butyl-7-oxabicyclo[2.2.1]hept-2-yl]methoxy]pentanoic acid Following the procedure of Examples 1 and 2 except substituting the above part C alcohol for the alcohol used in Example 1 Part G, the title compound is obtained.

EXAMPLE 118

(1α,2β,3β,4α)-5-[[[3-[4-(Benzyloxy)butyl-7-oxabicyclo[2.2.1]hept-2-yl]methyl]thio]pentanoic acid Following the procedure of Examples 117 and 16 except substituting the Example 117 Part C alcohol for the Example 16 Part A alcohol and substituting benzyl mesylate for hexyl mesylate, the title compound is obtained.

EXAMPLE 119

(1α,2β,3β,4α)-5-[[3-[4-(Cyclohexylthio)butyl]-7-oxabicyclo[2.2.1]hept-2-yl]methoxy]pentanoic acid Following the procedure of Examples 117 and 17 except substituting the Example 117 Part C alcohol for the Example 15 Part C alcohol and substituting cyclohexylmercaptan for 1-hexanethiol, the title compound is obtained.

EXAMPLE 120

(1α,2β,3β,4α)-5-[[[3-(4-(Hexylthio)butyl]-7-oxabicyclo[2.2.1]hept-2-yl]methyl]thio]pentanoic acid

A.
(1α,2β,3β,4α)-5-[[[3-(3-Oxo)propyl-7-oxabicyclo[2.2.1]hept-2-yl]methyl]thio]pentanoic acid, methyl ester Following the procedure of Example 18 Part B except substituting (1α,2β,3β,4α)-5-[[[3-(2-oxo)ethyl-7-oxabicyclo[2.2.1]hept-2-yl]methyl]thio]pentanoic acid, methyl ester for (1α,2β,3β,4α)-5-[[[3-formyl-7-oxabicyclo[2.2.1]hept-2-yl]methyl]thio]pentanoic acid, methyl ester, the title A compound is obtained.

B.
(1α,2β,3β,4α)-5-[[[3-(4-Oxo)butyl-7-oxabicyclo[2.2.1]hept-2-yl]methyl]thio]pentanoic acid, methyl ester Following the procedure of Example 18 Part B except substituting the aldehyde from Part A above for (1α,2β,3β,4α)-5-[[[3-formyl-7-oxabicyclo[2.2.1]hept-2-yl]methyl]thio]pentanoic acid, methyl ester, the title B aldehyde is obtained.

C.
(1α,2β,3β,4α)-5-[[[3-(4-Hydroxybutyl)-7-oxabicyclo[2.2.1]hept-2-yl]methyl]thio]pentanoic acid, methyl ester Following the procedure of Example 18 Part C except substituting the title B aldehyde for (1α,2β,3β,4α)-5-[[[3-(2-oxo)ethyl-7-oxabicyclo[2.2.1]hept-2-yl]methyl]thio]pentanoic acid, methyl ester, the title C alcohol is obtained.

D.
(1α,2β,3β,4α)-5-[[[3-[4-(Hexylthio)butyl]-7-oxabicyclo[2.2.1]hept-2-yl]methyl]thio]pentanoic acid Following the procedure of Examples 3 and 4 except substituting the above Part C alcohol for the alcohol used in Example 3, the title compound is obtained.

EXAMPLE 121

(1α,2β,3β,4α)-4-[2-[3-[4-(Hexyloxy)butyl]-7-oxabicyclo[2.2.1]hept-2-yl]ethoxy]butanoic acid Following the procedure of Examples 117 and 19 except substituting the Example 19 Part B aldehyde for the aldehyde used in Example 117 Part A, the title compound is obtained.

EXAMPLE 122

(1α,2β,3β,4α)-5-[[2-[3-[4-(Hexyloxy)butyl]-7-oxabicyclo[2.2.1]hept-2-yl]ethyl]thio]pentanoic acid Following the procedure of Examples 117 and 20 except substituting the Example 20 Part B aldehyde for the aldehyde used in Example 117 Part A, the title compound is obtained.

EXAMPLE 123

(1α,2β,3β,4α)-4-[[2-[3-[4-(Hexylthio)butyl]-7-oxabicyclo[2.2.1]hept-2-yl]ethyl]thio]pentanoic acid Following the procedure of Examples 120 and 22 except substituting the Example 22 Part A aldehyde for the aldehyde used in Example 120 Part A, the title compound is obtained.

EXAMPLE 124

(1α,2β,3β,4α)-5-[[3-[(Hexylsulfinyl)methyl]-7-oxabicyclo[2.2.1]-hept-2-yl]methoxy]pentanoic acid, methyl ester and (1α,2β,3β,4α)-5-[[3-(Hexylsulfonyl)methyl-7-oxabicyclo[2.2.1]hept-2-yl]methoxy]pentanoic acid, methyl ester To a solution of 668 mg (1.72 mmol) of (1α,2β,3β,4α)-5-[[3-[(hexylthio)methyl]-7-oxabicyclo[2.2.1]hept-2-yl]methoxy]pentanoic acid, methyl ester (prepared as described in Example 1) in 6.78 ml of methanol at 0° C. is added dropwise over 4 minutes 8.37 ml of 0.5M aqueous sodium periodate solution. Tetrahydrofuran (2 ml) is then added and the resulting reaction mixture is stirred at room temperature for 15 hours. A white precipitate is removed by filtration and washed with ether (3×50 ml). The filtrate is washed with 60 ml of saturated aqueous NaHCO₃ solution and dried over anhydrous magnesium sulfate. Concentration in vacuo affords 648 mg of an oily crude product. This is chromatographed on 54.16 g of silica gel 60 using 0.5–1.0% CH₃OH to give the title compounds.

EXAMPLE 125

(1α,2β,3β,4α)-5-[[3-[(Hexylsulfonyl)methyl]-7-oxabicyclo[2.2.1]hept-2-yl]methoxy]pentanoic acid To a stirred solution of 165 mg (0.39 mmole) of the Example 124 sulfonyl compound in 20.3 ml of THF and 3.09 ml of H₂O under argon is added 3.90 ml of 1N aqueous lithium hydroxide solution. This mixture is purged with argon vigorously for 10 minutes and stirred at room temperature for 6 hours. The reaction mixture is acidified to pH 4 by addition of 1N aqueous HCl solution and poured into 30 ml of saturated NaCl solution. The resulting solution is saturated with solid NaCl and extracted with EtOAc (4×50 ml). The combined EtOAc extracts are dried (MgSO₄), filtered and concentrated in vacuo to give 165 mg of crude acid which is purified by flash chromatography to obtain 145 mg of pure acid.

EXAMPLE 126

(1α,2β,3β,4α)-7-[[[3-[(Hexylsulfinyl)methyl]-7-oxabicyclo[2.2.1]hept-2-yl]methoxy]pentanoic acid To a stirred solution of 142 mg (0.35 mmol) of Example 124 ester and sulfinyl ester in 27.0 ml of THF and 4.11 ml of H₂O under argon is added 5.19 ml of 1N aqueous lithium hydroxide solution. This mixture is purged with argon vigorously for 10 minutes and stirred at room temperature for 6 hours. The reaction mixture is acidified to pH 4 by addition of 1N aqueous HCl solution and poured into 50 ml of saturated NaCl solution. The resulting solution is saturated with solid NaCl and extracted with EtOAc (4×100 ml). The combined EtOAc extracts are dried (MgSO$_4$), filtered and concentrated in vacuo to give crude acid which is purified by flash chromatography.

EXAMPLES 127 TO 136

Following the procedures as outlined in the specification and as described in the working Examples, the following compounds may be prepared.

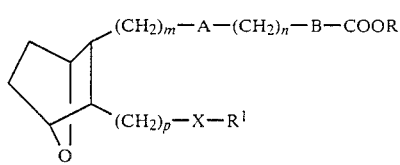

| Ex. No. | m | A | n | B | p | X | R$^1$ |
|---|---|---|---|---|---|---|---|
| 127 | 1 | O | 2 | — | 1 | S | C$_3$H$_7$ |
| 128 | 2 | S | 1 | CH=CH | 2 | S | C$_6$H$_5$ |
| 129 | 1 | S | 4 | CH=CH | 3 | O | C$_6$H$_4$(CH$_2$)$_2$— |
| 130 | 2 | O | 5 | — | 2 | O | (cyclopentyl) |
| 131 | 1 | O | 3 | CH=CH | 4 | S(=O) | (cyclopentyl)–CH$_2$— |
| 132 | 2 | S | 6 | — | 5 | O | (cyclohexyl) |
| 133 | 1 | O(=S=O) | 7 | CH=CH | 3 | O(=S=O) | CH$_2$=CH—CH$_2$— |
| 134 | 2 | S | 8 | — | 2 | O | CH$_3$CH$_2$CHCH$_2$— |
| 135 | 1 | O(=S) | 6 | CH=CH | 1 | O(=S) | C$_6$H$_{13}$ |
| 136 | 2 | O | 5 | CH=CH | 2 | S | C$_4$H$_9$ |

What is claimed is:

1. A compound of the structure

including all stereoisomers thereof, wherein A is O or

B is a single bond or —CH=CH—; m is 1 or 2; n is 1 to 8; p is 1 to 5; X is O or

wherein q is 0, 1 or 2 when A is O, and when either A or X is S then the other may not be $$\overset{S}{\underset{(O)_q}{\|}}$$

wherein q is 1 or 2; R is H, lower alkyl, alkali metal or tris(hydroxymethyl)aminomethane; and R$^1$ is lower alkyl, aryl, arylalkyl, cycloalkyl, cycloalkylalkyl or lower alkenyl, wherein the term lower alkyl or alkyl by itself or as part of another group contains 1 to 12 carbons and is unsubstituted or substituted with halo, trifluoromethyl, alkoxy, aryl, alkyl-aryl, haloaryl, cycloalkyl or alkylcycloalkyl;

the term aryl by itself or as part of another group contains 6 to 10 carbons and is unsubstituted or substituted with 1 or 2 lower alkyl groups, 1 or 2 halogens and/or 1 or 2 lower alkoxy groups;

the term cycloalkyl by itself or as part of another group contains 3 to 12 carbons and is unsubstituted or substituted with 1 or 2 halogens, 1 or 2 lower alkyl groups and/or 1 or 2 lower alkoxy groups;

the term lower alkenyl by itself or as part of another group contains 2 to 12 carbons; and the term (CH$_2$)$_m$ includes 1 or 2 carbons in the normal chain, the term (CH$_2$)$_n$ includes 1 to 8 carbons in the normal chain and the term (CH$_2$)$_p$ includes 1 to 5 carbons in the normal chain, and the terms (CH$_2$)$_m$, (CH$_2$)$_n$ and (CH$_2$)$_p$ may be unsubstituted or include one or more lower alkyl substituents.

2. The compound as defined in claim 1 wherein A is O and X is O.

3. The compound as defined in claim 1 wherein A is S and X is O.

4. The compound as defined in claim 1 wherein m is 1 and p is 1.

5. The compound as defined in claim 1 wherein n is 3 to 5.

6. The compound as defined in claim 1 wherein B is a single bond, m is 1, A is O or S, p is 1, n is 3 to 5, R is H and R$^1$ is lower alkyl.

7. The compound as defined in claim 1 wherein R$^1$ is butyl, pentyl, hexyl or heptyl including all isomers thereof.

8. The compound as defined in claim 1 having the name (1α,2β,3β,4α)-5-[[3-[(hexyloxy)methyl]-7-oxabicyclo[2.2.1]hept-2-yl]methoxy]pentanoic acid or the hexyl ester thereof, including all stereoisomers thereof.

9. The compound as defined in claim 1 having the name (1α,2β,3β,4α)-5-[[[3-[(hexyloxy)methyl]-7-oxabicyclo[2.2.1]hept-2-yl]methyl]thio]pentanoic acid or the methyl and/or ether esters thereof, including all stereoisomers thereof.

10. A method of inhibiting arachidonic acid-induced platelet aggregation and bronchoconstriction, which comprises administering to the circulatory system of a mammalian host an effective amount of a compound as defined in claim 1 or a pharmaceutically acceptable salt thereof.

11. The method as defined in claim 10 wherein said compound is administered in an amount within the range of from about 1 to about 100 mg/kg.

12. A composition for inhibiting arachidonic acid-induced platelet aggregation and bronchoconstriction comprising an effective amount of a compound as defined in claim 1 or a pharmaceutically acceptable salt thereof, and a pharmaceutically acceptable carrier therefor.

13. A method of inhibiting platelet aggregation which comprises administering to a mammalian host an effective amount of a compound as defined in claim 1 or a pharmaceutically acceptable salt thereof.

14. A method of inhibiting bronchoconstriction associated with asthma, which comprises administering to a mammalian host an effective amount of a compound as defined in claim 1 or a pharmaceutically acceptable salt thereof.

15. A method for treating peripheral vascular disease, which comprises topically or systemically administering to a mammalian host an effective amount of a compound as defined in claim 1 or a pharmaceutically acceptable salt thereof.

* * * * *

UNITED STATES PATENT AND TRADEMARK OFFICE
CERTIFICATE OF CORRECTION

PATENT NO. : 4,550,120
DATED : October 29, 1985
INVENTOR(S) : Jagabandhu Das et al.

It is certified that error appears in the above-identified patent and that said Letters Patent is hereby corrected as shown below:

Column 3, line 60, structure IV should read

-- 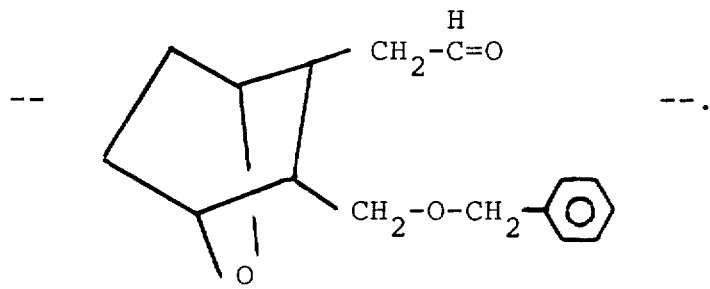 --.

Column 19, line 39, insert --C.--
Column 22, line 50, "$R_5$" should read --$R_f$--.
Column 31, line 18, "[[3" should read --[[3--.
Column 35, line 6, " ]7 " should read --]-7--.
Column 35, line 7, "]2" should read --]-2--.
Column 35, line 34, "]2" should read --]-2--.
Column 36, line 16, "2pentenoic" should read --2-pentenoic--.
Column 36, line 56, "]2" should read --]-2--.

UNITED STATES PATENT AND TRADEMARK OFFICE
CERTIFICATE OF CORRECTION

PATENT NO. : 4,550,120

DATED : October 29, 1985

INVENTOR(S) : Jagabandhu Das et al.

It is certified that error appears in the above-identified patent and that said Letters Patent is hereby corrected as shown below:

```
Column 37, line 48, "]2" should read --]-2--.
Column 38, line 52, "(3" should read --[3--.
Column 52, line 61, "ether" should read --ethyl--.
```

Signed and Sealed this

Twenty-eighth Day of October, 1986

[SEAL]

*Attest:*

DONALD J. QUIGG

*Attesting Officer*　　　*Commissioner of Patents and Trademarks*